(12) United States Patent
Yousaf

(10) Patent No.: US 9,080,144 B2
(45) Date of Patent: Jul. 14, 2015

(54) COMPOSITIONS AND METHODS FOR PROMOTING LIPOSOMAL AND CELLULAR ADHESION

(71) Applicant: Muhammad Naveed Yousaf, Mississauga (CA)

(72) Inventor: Muhammad Naveed Yousaf, Mississauga (CA)

(73) Assignee: Muhammad Naveed Yousaf, Mississauga (CA)

( * ) Notice: Subject to any disclaimer, the term of this patent is extended or adjusted under 35 U.S.C. 154(b) by 89 days.

(21) Appl. No.: 13/890,613

(22) Filed: May 9, 2013

(65) Prior Publication Data

US 2013/0302891 A1 Nov. 14, 2013

Related U.S. Application Data

(60) Provisional application No. 61/645,217, filed on May 10, 2012.

(51) Int. Cl.
| | | |
|---|---|---|
| *A61K 8/14* | (2006.01) | |
| *C12N 5/00* | (2006.01) | |
| *A61K 8/98* | (2006.01) | |
| *A61Q 19/00* | (2006.01) | |

(52) U.S. Cl.
CPC ............ *C12N 5/0006* (2013.01); *A61K 8/14* (2013.01); *A61K 8/981* (2013.01); *A61Q 19/00* (2013.01); *A61K 2800/10* (2013.01); *A61K 2800/805* (2013.01); *C07K 2317/24* (2013.01); *C07K 2317/31* (2013.01); *C07K 2317/569* (2013.01); *C07K 2317/76* (2013.01); *C07K 2317/92* (2013.01); *C07K 2317/94* (2013.01)

(58) Field of Classification Search
CPC ........................................................ A61K 8/14
USPC ........................................................ 435/375
See application file for complete search history.

(56) References Cited

U.S. PATENT DOCUMENTS

| | | | |
|---|---|---|---|
| 4,861,597 A | 8/1989 | Kida et al. | |
| 6,417,326 B1 * | 7/2002 | Cullis et al. | 530/324 |
| 2012/0100077 A1 | 4/2012 | Hoffman et al. | |

OTHER PUBLICATIONS

Faiss et al., 2004, Eur. Biophysics J., 33, 555-561.*
Wilson, J.T. et al., "Noncovalent Cell Surface Engineering with Cationic Graft Copolymers", J. Am. Chem. Soc., 2009, 131, 18228-18229.
Dutta, Debjit, et al, "Engineering Cell Surfaces via Liposome Fusion", Bioconjugate Chemistry, Nov. 5, 2011, pp. 2423-2433.
Dutta, Debjit, et al., "Synthetic Chemoselective Rewiring of Cell Surfaces: General of Three-Dimensional Tissue Surfaces", Journal of the American Chemical Society, 2011, 133, 8704-8713.

* cited by examiner

*Primary Examiner* — Sharmila G. Landau
*Assistant Examiner* — Sheridan Macauley
(74) *Attorney, Agent, or Firm* — Bereskin & Parr LLP/S.E.N.C.R.L., s.r.l.; Patricia Folkins

(57) ABSTRACT

The present application describes compounds, compositions and methods for incorporating chemoselective and bio-orthogonal complementary functional groups into liposomes. The present application also describes various uses of these modified liposomes including for tethering the chemoselective and bio-orthogonal complementary functional groups from cell surfaces by liposome delivery toward the goal of rewiring the cell surface.

12 Claims, 9 Drawing Sheets

COMPOSITIONS AND METHODS FOR PROMOTING LIPOSOMAL AND CELLULAR ADHESION

The present application relates to the incorporation of complementary, bio-orthogonal reactive functional groups into liposomes and the use of the resulting compositions for promoting liposomal and cellular adhesion.

BACKGROUND OF THE APPLICATION

Cells that make up tissues and organs exist and communicate within a complex, three-dimensional (3D) environment. The spatial orientation and distribution of extracellular matrix (ECM) components directly influences the manner in which cells receive, integrate, and respond to a range of input signals.[1] As such, cellular interactions with ECM molecules and/or other cells have been extensively investigated for fundamental studies in development, cell motility, differentiation, apoptosis, paracrine signaling, and applications in tissue engineering.[2,3] There has been tremendous effort toward the design and fabrication of 3D scaffolds that mimic ECM properties and induce tissue formation in vitro, utilizing various biomaterials, biodegradable polymers,[4] collagen,[5] and hydrogels.[6,7] Among the major challenges facing the use of these technologies for tissue engineering are the abilities to force contact between multiple cell types in 3D to control the spatial and temporal arrangement of cellular interactions and tailor and mold the biomaterial to recapitulate the 3D, in vivo environment under laboratory constraints. Without the use of engineered scaffolds in culture, most cells are unable to form the necessary higher-order 3D structure required for the anatomical mimicry of tissue and are limited to random migration, generating two-dimensional (2D) monolayers. As a result, several approaches, including the use of dielectrophoretic forces,[8,9] laser-guided writing,[10-12] surface manipulation,[13] and a number of lithographic printing techniques[14-17] have been integrated with 3D scaffold designs to produce multi-type cellular arrays[9,11,17,18] or 3D cell clusters or spheroids.[7,8,13] In a recent study, 3D aggregates consisting of multiple cell types were formed within a hydrogel matrix through DNA hybridization after cell surfaces were engineered with complementary short oligonucleotides via a metabolic labeling approach.[7] However, for some applications, the presentation of cell-surface DNA may not be stable for extended time periods in cell culture or in vivo.

Cell-surface engineering methodologies have primarily been of interest in molecular biology. As such, biosynthetic approaches have been employed to introduce different functional groups on cell surfaces. In a pioneering study, an unnatural derivative of N-acetyl-mannosamine, which bears a ketone group, was converted to the corresponding sialic acid and metabolically incorporated onto cell-surface oligosaccharides, resulting in the cell surface display of ketone groups.[19] However, metabolic or genetic methods may alter many of the biochemical pathways required for normal cell function and not all cell lines possess this metabolic machinery. Thus, there is a growing demand for general tools that can provide simple alternatives to the complex genetic and biosynthetic methods. Other approaches to cell-surface engineering have also been undertaken to incorporate a functional group into a target biomolecule, such as an endogenous protein, utilizing a cell's biosynthetic machinery.[20,21] These strategies aim to produce a site that can then be covalently modified with its delivered counterpart or probe. However, most of these protein-based tags are large and bulky and become problematic when interacting with the other glycans and biomolecules on the cell sufface.[22,23] Additionally, the perturbation of cellular physiology with biomolecules at the cell surface may result in the interference of significant biochemical pathways or cellular functions.[24,25].

Membrane fusion processes are ubiquitous in biology and span multi-cellular communication, extracellular signaling, the reconstruction of damaged organelles, and integration of cells into complex tissues and organs.[26] As a result, there has been much interest in developing model systems to mimic biological membranes to investigate the mechanisms of fusion and for use in various biotechnological applications. For example, cells secrete and display proteins and lipids during vesicle trafficking events that either diffuse into the ECM or become components of the cell membrane after fusion.[27] Naturally, lipid vesicles provide an ideal platform for such studies and have been widely used to examine various membrane-related processes, including fusion.[28-39] In order for fusion to occur, the membranes must be brought into close proximity, followed by bilayer destabilization.[31] Fusion of such lipid vesicles or liposomes can be initiated by using divalent cations, polycations,[32] positively charged amino acids[33] and membrane-disrupting peptides.[34,35] Historically, synthetic chemical agents have also been employed to fuse vesicle membranes[36-39] through non-specific interactions. However, recent efforts to improve selectivity and control over vesicle fusion have been achieved through the use of small, synthetic molecular recognition pairs.[40-41] Since vesicle fusion is a natural process and has been shown to influence the construction of cells into multicellular organisms, much research has focused on using liposomes to deliver cargoes, reagents, nanomaterials, and therapeutic agents to cells.

Noncovalent cell-surface engineering strategies via cationic graft copolymer adsorption and a fluorescent cell labeling technique via cationic and aromatic lipid fusion have been previously reported.[42]

SUMMARY OF THE APPLICATION

The present application describes compounds, compositions and methods for incorporating chemoselective and bio-orthogonal complementary functional groups, such as ketone and oxyamine groups, into liposomes. In one embodiment of this application, alkyl ketone and oxyamine molecules spontaneously inserted into separate liposomes upon synthesis. When these two types of liposomes were mixed, chemical recognition occurred, producing stable oxime bonds under physiological conditions. The liposomes combined in this manner reacted chemoselectively to form an interfacial, covalent oxime linkage, resulting in liposome docking and adhesion. Adhered liposomes either fused or formed multi-adherent structures.

Accordingly, the present application includes a mixture comprising a plurality of liposomes of type A and a plurality of liposomes of type B, wherein the liposomes of type A comprise a reactive functional group that reacts with a reactive functional group comprised in the liposomes of type B to form a chemical interaction that results in adhesion of the liposomes of type A and the liposomes of type B.

In an embodiment of the application, the adhesion of the liposomes of type A and the liposomes of type B results in formation of multi-adherent liposomes, the partial fusion of liposomes of type A and the liposomes of type B and/or the complete fusion of the liposomes of type A and type B.

It is an embodiment of the application that the reactive functional groups in the liposomes of type A and B are bio-orthogonal. In an embodiment, the reactive functional group is comprised in an amphipatic molecule wherein the reactive functional group is located in the hydrophilic portion of the molecule. In a further embodiment of the application, the reactive functional group in the liposomes of type A is a ketone and the reactive functional group in the liposomes of type B is an oxyamine. Accordingly, in another embodiment the present application includes a liposome comprising an amphipatic molecule wherein the hydrophilic portion of the amphipatic molecule comprises a ketone. In a further embodiment the present application includes a liposome comprising an amphipatic molecule wherein the hydrophilic portion of the amphipatic molecule comprises an oxyamine. In a specific embodiment, the amphipatic molecule comprising a ketone in the hydrophilic portion is $R^1C(O)R^2$ and the amphipatic molecule comprising an oxyamine in the hydrophilic portion is $R^3$—O—$NH_2$, wherein $R^1$ and $R^3$ are independently selected from $C_{6-30}$alkyl and $C_{6-30}$alkenyl and $R^2$ is $C_{1-2}$alkyl.

In an embodiment of the application, aside from the amphipatic molecule comprising a reactive functional group, the liposomes further comprise any suitable amphipatic molecule, or mixture of molecules, that form liposomes. In general, liposome-forming amphipatic molecules are lipids, in particular phospholipids. In a further embodiment, the amphipatic molecules are selected based on the proposed use of the liposome.

In yet another embodiment, the liposomes further comprise other functional molecules, such as fluorescent molecules, dyes and/or other indicator molecules, so that when the liposomes of type A and type B are fused, a physical change, such as a change in fluorescence, color or smell, occurs.

The present application also includes a method for promoting adhesion of liposomes comprising contacting a plurality of liposomes of type A with a plurality of liposomes of type B, wherein the liposomes of type A comprise a reactive functional group that reacts with a reactive functional group comprised in the liposomes of type B to form a chemical interaction that results in the adhesion of the liposomes of type A and the liposomes of type B.

The present application also describes compounds, compositions and methods for tethering chemoselective and bio-orthogonal complementary functional groups, such as ketone and oxyamine groups, from cell surfaces by liposome delivery toward the goal of rewiring the cell surface. In one embodiment, the liposomes described above comprising ketone and oxyamine groups were cultured with various cell types resulting in membrane fusion and the display of ketones and oxyamines on the cell surface in a manner such that they were available for further chemical manipulation. Therefore the synthetic ketone and oxyamine molecules fused on the cell membrane serve as cell-surface receptors, providing tools for the attachment of other functional materials, biomolecules, and probes on the cell surface. In sum, liposome fusion to cell membranes is employed herein as a method to deliver small chemical functional groups to tailor the cell membrane for subsequent bio-orthogonal and chemoselective ligation reactions.

The present application therefore includes a method for promoting the adhesion of cells comprising:
(a) contacting a first cell population with a liposome of type A under conditions for the fusion of the liposome of type A with the first cell population;
(b) contacting a second cell population with a liposome of type B under conditions for the fusion of the liposome of type B with the second cell population; and
(c) contacting the fused first cell population with the fused second cell population,
wherein the liposomes of type A comprise a reactive functional group that reacts with a reactive functional group comprised in the liposomes of type B to form a chemical interaction that results in the adhesion of the first and second cell populations.

Thus, the present application includes a methodology that combines cell-surface modification, without the use of molecular biology techniques or biomolecules, and a simple, stable bio-orthogonal conjugation bottom-up approach that is capable of directing tissue formation and that will greatly benefit a range of medical applications. This platform should also find wide use in studying fundamental cell behavior and provide a range of new tools for tissue engineering and biomedical applications.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The present application will now be described in greater detail with reference to the drawings in which:

FIG. 3 (Bottom) shows a general schematic and images for cell-surface tailoring using liposome fusion and chemoselective oxime chemistry. (d) Keto-LUVs (5, 3 mM) were added and fused with the cells to display these groups from the cell surface (9). Addition of rhod-oxyamine (8, 0.7 mM in $H_2O$, 2 min) resulted in chemoselective oxime formation and red fluorescent labeling of the cells. Images display (e) control fbs where liposomes not displaying ketones were fused to the membrane (2 h) and rhod-oxyamine was added and no fluorescence was observed and (f) fluorescently labeled cells after ketone-functionalized liposomes were fused to fbs (2 h) and cells were incubated with rhod-oxyamine. Scale bars for b and c (collectively) and d and e (collectively) represent 50 and 30 μm, respectively.

DETAILED DESCRIPTION OF THE APPLICATION

I. Definitions

Figure 1:
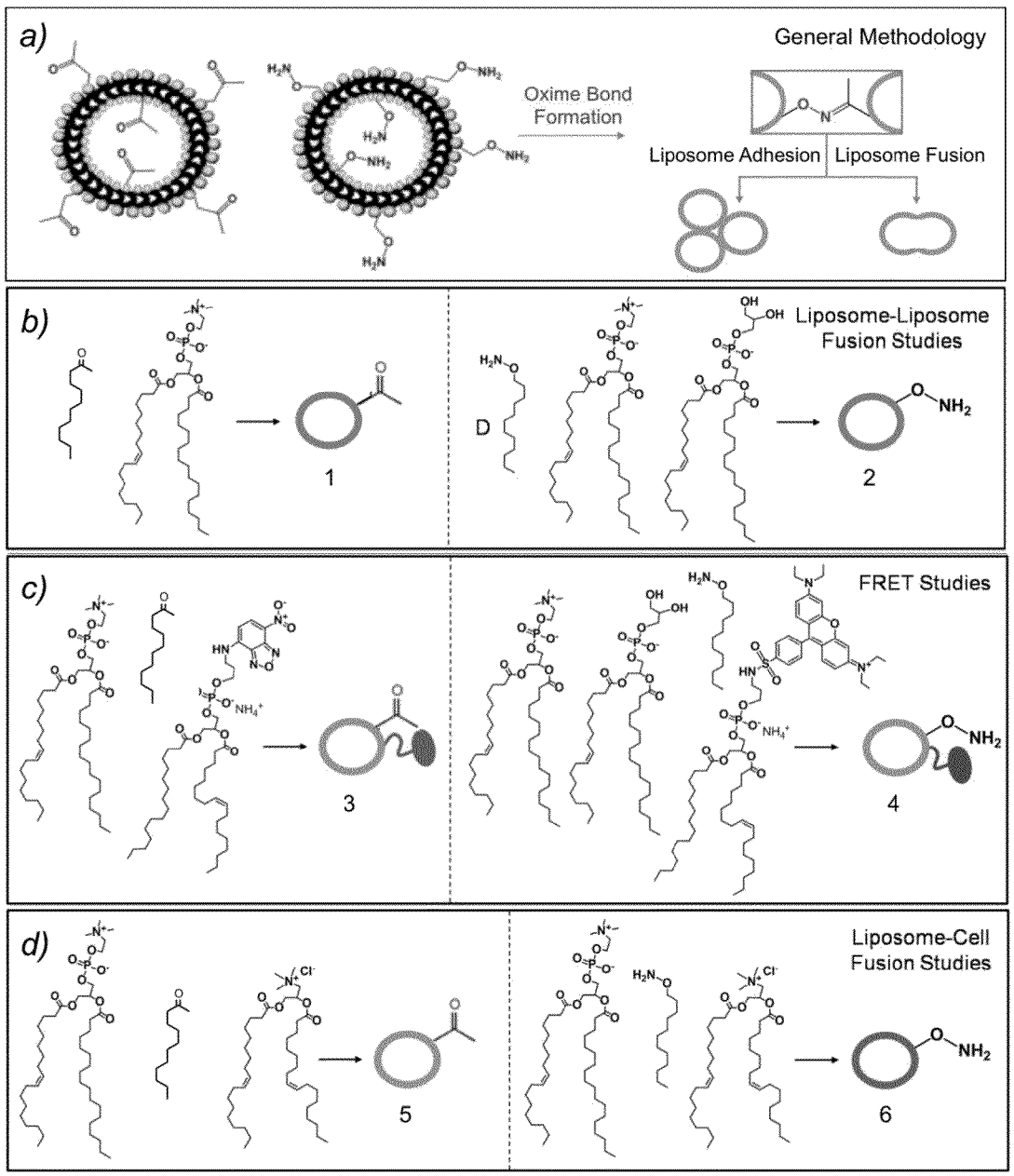
FIG. 1 shows a general schematic and corresponding lipid components for the formation of fused and adhered liposomes based on chemoselective oxime conjugation. (a) When mixed, ketone- and oxyamine-tethered liposomes react chemoselectively to form an interfacial, covalent oxime linkage, resulting in liposome docking and adhesion. Docked liposomes either fuse or form multi-adherent structures. (b) Dodecanone molecules were incorporated into neutral, POPC at a ratio of 5:95 to form keto-LUVs (1), while O-dodecyloxyamine molecules were incorporated into POPC and negatively charged, POPG at a ratio of 5:75:20 to form oxyamine-LUVs (2). These liposomes were used for liposome-liposome fusion studies. (c) Dodecanone molecules were incorporated into POPC and fluorescence donor, NBD-PE at a ratio of 5:93:2 to form keto-NBD-PE LUVs (3). O-Dodecyloxyamine molecules were incorporated into POPC, POPG, and fluorescence acceptor, rhod-PE at a ratio of 5:73:20:2 to form oxyamine-rhod-PE LUVs (4). These liposomes were used for FRET studies. (d) Dodecanone molecules were incorporated into POPC and positively charged, DOTAP at a ratio of 5:97:2 to form ketone-presenting liposomes (5). O-Dodecyloxyamine molecules were incorporated into POPC and DOTAP at a ratio of 5:93:2 to form oxyamine-presenting liposomes (6). These liposomes were used for cell-liposome fusion studies.

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a lipid" should be understood to present certain aspects with one lipid, or two or more additional lipids.

In embodiments comprising an "additional" or "second" component, such as an additional or second lipid, the second component as used herein is chemically different from the other components or first component. A "third" component is different from the other, first, and second components, and further enumerated or "additional" components are similarly different.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "bio-orthogonal" as used herein refers to non-native, non-perturbing chemical functional groups that are introduced into naturally occurring, living systems and are modified in these living systems through selective reactions that do not interfere with any other chemical moieties in the natural surroundings.

The term "amphiphatic" or "amphiphilic" refers to a compound comprising both hydrophilic (water loving) and lipophilic (fat loving) portions.

The term "liposomes" as used herein refers to artificially prepared vesicles, the surface of which is a bilayer formed from amphiphatic molecules.

The term "reactive functional group" as used herein refers to a group of atoms or a single atom that will react with another group of atoms or a single atom (so called "complementary functional group") under bio-orthogonal reaction conditions to form a chemical interaction between the two groups or atoms.

The term "reacts with" as used herein generally means that there is a flow of electrons or a transfer of electrostatic charge resulting in the formation of a chemical interaction.

The term "chemical interaction" as used herein refers to the formation of either a covalent of ionic bond between the reactive functional groups. The chemical interaction is one that is strong enough to promote the adhesion of liposomes or cells.

The term "adhere" or "adhesion" as used herein means to bring two or more entities, such as two or more liposomes or two or more cells, into close proximity to each other and to remain in contact with each other. The adhered liposomes may remain as separate entities or, their membranes may destabilize and fuse together to result in the formation of a single liposome. The adhered cells may communicate with each other and may divide and multiply forming, for example, tissues.

The term "alkyl" as used herein means straight or branched chain, saturated alkyl groups. The number of carbon atoms in the chain is defined by the $C_{\#-\#}$ prefix preceding the term. For example, the term $C_{6-30}$alkyl means an alkyl group having 6, 7, 8, 9, 10, 11, 12, 13, 14, 15, 16, 17, 18, 19, 20, 21, 22, 24, 25, 26, 27, 28, 29 or 30 carbon atoms.

The term "alkenyl" as used herein means straight or branched chain, unsaturated alkyl groups containing one or more, suitably one or three, more suitable one or two, double bonds. The number of carbon atoms in the chain is defined by the $C_{\#-\#}$ prefix preceding the term. For example, the term $C_{6-30}$alkyl means an alkenyl group having 6, 7, 8, 9, 10, 11, 12, 13, 14, 15, 16, 17, 18, 19, 20, 21, 22, 23, 24, 25, 26, 27, 28, 29 or 30 carbon atoms.

The term "oxyamine" as used herein refers to the functional group "—O—NH$_2$".

The term "ketone" refers to the functional group "—C(O)—".

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

II. Liposome Adhesion

The present application includes a mixture comprising a plurality of liposomes of type A and a plurality of liposomes of type B, wherein the liposomes of type A comprise a reactive functional group that reacts with a reactive functional group comprised in the liposomes of type B to form a chemical interaction that results in the adhesion of the liposomes of type A and the liposomes of type B.

In an embodiment of the application, the adhesion of the liposomes of type A and the liposomes of type B results in formation of multi-adherent liposomes, the partial fusion of liposomes of type A and the liposomes of type B and/or the complete fusion of the liposomes of type A and type B. In an further embodiment, the adhesion of the liposomes of type A and the liposomes of type B results in the complete fusion of the liposomes of type A and the liposomes of type B.

As would be understood by a person skilled in the art, the reactive functional groups in the liposomes of type A differ, but are complementary to, the reactive functional groups in the liposomes of type B. By complementary it is meant that the reactive functional groups interact, or react with each other, to form a chemical interaction that is strong enough to promote the adhesion of the two types of liposomes to each other. In an embodiment, the chemical interaction is a covalent bond or an ionic bond. In another embodiment, the chemical interaction is a covalent bond.

It is an embodiment of the application that the reactive functional groups in the liposomes of type A and B are bio-orthogonal. Examples of complementary, bio-orthogonal pairs of reactive functional groups include, but are not limited to:

(1) ketones and oxyamines which react to form an oxime;
(2) ketones and hydrazines which react to form a hydrazone;
(3) dienes and dienophiles which react to form a six membered ring (Diels Alder reaction); and
(4) azides and alkynes which react to form a triazole (Huisgen reaction).

It is an embodiment that the complementary, bio-orthogonal pair of reactive functional groups are ketones and oxyamines which react to form an oxime.

In an embodiment, the reactive functional group is comprised in an amphiphatic molecule wherein the reactive functional group is located in the hydrophilic portion of the molecule. In an embodiment, the reactive functional group forms the hydrophilic portion of the amphiphatic molecule and the lipophilic portion of the amphiphatic molecule is a long hydrocarbon chain, optionally comprising one or more double bonds.

In a further embodiment of the application, the reactive functional group in the liposomes of type A is a ketone and the reactive functional group in the liposomes of type B is an oxyamine. Accordingly, in another embodiment the present application includes a liposome comprising an amphiphatic molecule wherein the hydrophilic portion of the amphiphatic molecule comprises a ketone. In a further embodiment, the present application includes a liposome comprising an amphiphatic molecule wherein the hydrophilic portion of the amphiphatic molecule comprises an oxyamine. In a specific embodiment, the amphiphatic molecule comprising a ketone in the hydrophilic portion is $R^1C(O)R^2$ and the amphiphatic molecule comprising an oxyamine in the hydrophilic portion is $R^3$—O—$NH_2$, wherein $R^1$ and $R^3$ are independently selected from $C_{6-30}$alkyl and $C_{6-30}$alkenyl and $R^2$ is $C_{1-2}$alkyl.

In a further embodiment of the application, the reactive functional group in the liposomes of type A is a ketone and the reactive functional group in the liposomes of type B is a hydrazine. Accordingly, in another embodiment the present application also includes a liposome comprising an amphiphatic molecule wherein the hydrophilic portion of the amphiphatic molecule comprises a hydrazine. In a specific embodiment, the amphiphatic molecule comprising a hydrazine in the hydrophilic portion is $R^4$—NH—$NH_2$, wherein $R^4$ is $C_{6-30}$alkyl.

In a further embodiment of the application, the reactive functional group in the liposomes of type A is an azide and the reactive functional group in the liposomes of type B is an alkyne. Accordingly, in another embodiment the present application includes a liposome comprising an amphiphatic molecule wherein the hydrophilic portion of the amphiphatic molecule comprises an azide. In a further embodiment, the present application includes a liposome comprising an amphiphatic molecule wherein the hydrophilic portion of the amphiphatic molecule comprises an alkyne. In a specific embodiment, the amphiphatic molecule comprising an azide in the hydrophilic portion is $R^5$—$N_3$ and the amphiphatic molecule comprising an oxyamine in the hydrophilic portion is $R^6$—C≡$CR^7$, wherein $R^5$ and $R^6$ are independently selected from $C_{6-30}$alkyl and $C_{6-30}$alkenyl and $R^7$ is H or $C_{1-2}$alkyl.

In a further embodiment of the application, the reactive functional group in the liposomes of type A is a diene and the reactive functional group in the liposomes of type B is a dienophile. Accordingly, in another embodiment the present application includes a liposome comprising an amphiphatic molecule wherein the hydrophilic portion of the amphiphatic molecule comprises a diene. In a further embodiment the present application includes a liposome comprising an amphiphatic molecule wherein the hydrophilic portion of the amphiphatic molecule comprises a dienophile. In an embodiment, the hydrophobic portion of these amphiphatic molecules is $C_{6-30}$alkyl.

The present application also includes compositions comprising one or more of the above-identified liposomes. In a further embodiment, the composition further comprises a solvent, diluent or carrier, such as an aqueous buffer.

In an embodiment, the present application includes a composition comprising the liposome comprising an amphiphatic molecule wherein the hydrophilic portion of the amphiphatic molecule comprises a ketone and a solvent, diluent or carrier. In a further embodiment, the present application also includes a composition comprising the liposome comprising an amphiphatic molecule wherein the hydrophilic portion of the amphiphatic molecule comprises an oxyamine and a solvent, diluent or carrier, such as an aqueous buffer.

In an embodiment of the application, aside from the amphiphatic molecule comprising a reactive functional group, the liposomes further comprise any suitable amphiphatic molecule, or mixture of molecules, that form liposomes. In general, liposome-forming amphiphatic molecules are lipids, in particular phospholipids. In a further embodiment, the liposome-forming amphiphatic molecules are selected based on the proposed use of the liposome. For example, if the liposomes are to be adhered to each other, the liposome-forming amphiphatic molecule is any suitable neutral, positively charged or negatively charged amphiphatic molecule or a mixture thereof. In general, to enhance the attraction between the two entities to be adhered or fused, the charges on each entity are opposite. Examples of suitable liposome-forming amphiphatic molecules are diverse and the present application is not limited to any specific type. Selection of the liposome-forming amphiphatic molecule and methods for the formation of liposomes are well within the skill of a person in the art.

For example, the liposomes are formed by dissolving the amphipatic molecule comprising a reactive functional group in an organic solvent and thoroughly combining the resulting solution with the liposome-forming amphipatic molecule(s), also dissolved in an organic solvent, followed by removal of all of the organic solvents. The dried samples are then reconstituted and brought to the desired concentration in an aqueous buffer solution, such as an aqueous buffer having a pH of about 7 to about 7.5. Sonication and warming may be used to obtain a clear solution of large unilamellar vesicles (LUVs).

As an example, the liposome-forming amphipatic molecule is selected from egg palmitoyl-oleoyl phosphatidylcholine (POPC, a neutral phospholipid), egg 1-palmitoyl-2-oleoyl-phophatidylglycerol (POPG, a negatively charged phospholipid) and 1,2,-dioleoyl-3-trimethylammonium-propane (DOTAP, a positively charged or cationic lipid).

In an embodiment, the amount of the amphipatic molecule comprising a reactive functional group in the liposome is about 1 mol % to about 10 mol %, or about 5 mol %. It is another embodiment that the liposome comprises about 90 mol % to about 99 mol % of a neutral lipid and, optionally, about 1 mol % to about 5 mol % of a charged lipid.

In another embodiment of the application, the liposomes of type A and type B further comprise fluorescent reporter molecules. In one embodiment, the fluorescent reporter molecules are incorporated into the liposome-forming amphipatic molecules.

In yet another embodiment, the liposomes further comprise other functional molecules, such as fluorescent molecules, dyes and/or other indicator molecules, so that when the liposomes of type A and type B are fused, a physical change, such as a change in color, fluorescence or smell, occurs. These functional molecules may be entrapped within the liposomes or be incorporated into the liposome-forming amphipatic molecules.

In a further embodiment of the application, the liposomes of type A and/or B further comprise biologically active agents, such as nucleic acids, proteins, peptides, small molecule drugs, carbohydrates and the like, and mixtures thereof, and fusion of the liposomes with the cell population results in the delivery of the biological agents into the cells. The biologically active agents may be entrapped within the liposome or may be incorporated into the liposome membrane.

In another embodiment of the application, the liposomes of type A and type B further comprise fluorescent reporter molecules. In one embodiment, the fluorescent reporter molecules are incorporated into the liposome-forming amphipatic molecules. When present in the liposome-forming amphipatic molecules, it is an embodiment that these molecules are incorporated into the liposomes in an amount of about 0.5 mol % to about 5 mol %, or about 2 mol %. As a representative example, the fluorescent phospholipids, egg 1,2-diphytanoyl-sn-glycero-3-phosphoethanolamine-N-(7-nitro-2-1,3-benzoxadiazol-4-yl) (ammonium salt) (NBD-PE), and egg 1,2-dipalmitoyl-sn-glycero-3-phosphoethanolamine-N-(lissamine rhodamine B sulfonyl) (ammonium salt) (Rhod-PE), are used. The incorporation of fluorescent reporter molecules into the liposome-forming amphipatic molecules allows for easy monitoring of liposome adhesion and fusion. For example, the use of NBD-PE (a fluorescence donor) in the liposomes of type A and rhod-PE (a fluorescence acceptor) in the liposomes of type B results in a gradual decrease in the donor emission peak and increase in the acceptor emission peak upon adhesion of the liposomes of type A to the liposomes of type B.

The present application also includes a method for promoting adhesion of liposomes comprising contacting a plurality of liposomes of type A with a plurality of liposomes of type B, wherein the liposomes of type A comprise a reactive functional group that reacts with a reactive functional group comprised in the liposomes of type B to form a chemical interaction that results in the adhesion of the liposomes of type A and the liposomes of type B.

The present application further includes kits or commercial packages for performing the method of promoting the adhesion of liposomes. In an embodiment, the kit or package comprises, in separate containers, a solution of a plurality of liposomes of type A and a solution of a plurality of liposomes of type B, wherein the liposomes of type A comprise a reactive functional group that reacts with a reactive functional group comprised in the liposomes of type B to form a chemical interaction that results in the adhesion of the liposomes of type A and the liposomes of type B, along with instructions for performing the method. In one embodiment, the kit or package further comprises separate means for forming bubbles with the each of the plurality of liposomes of type A and a plurality of liposomes of type B. Any means for forming bubbles may be used, such as any shaped device upon which a film of the solution comprising the liposomes of type A and the solution of the liposomes of type B can form and the user can apply a flow of a gas, such as air, to form bubbles. Examples of such means includes the typical bubble blowing devices that are found in children's bubble forming toy products. In an embodiment, the instructions include directions to form a bubble from each of the solutions of liposomes of types A and B and to bring the bubbles into contact with each other. In a further embodiment, each of the liposomes of type A and type B further comprise an indicator molecule, such as a dye, and contact of the bubbles of type A with the bubbles of type B results in a fused bubble having a different detectable property, such as a different colour. In an embodiment, these kits and commercial packages are used or sold as novelty items or toys.

III. Liposome Fusion to Cells

Liposome fusion to mammalian cell membranes was directed through the use of a cationic lipid and a molecular recognition pair for chemoselective ligation. In one embodiment, vesicles were tailored with ketone (dodecanone) or oxyamine (O-dodecyloxyamine) molecules, a neutral lipid, egg palmitoyl-oleoyl phosphatidylcholine (POPC), and a cationic lipid, 1,2-dioleoyl-3-trimethylammonium-propane (DOTAP). The resulting two vesicle populations were then integrated with mammalian cells in culture. Applications for this strategy, include, but are not limited to, small molecule delivery, cell-surface modification, and tissue engineering. By employing this membrane tailoring strategy, the assembly of 3D spheroid clusters and tissue-like structures were directed after culturing two cell populations functionalized with oxyamine- and ketone-containing groups. Because this method is general, bio-orthogonal, chemically stable, and non-cytotoxic, patterned multi-layered tissue-like structures of different geometric shapes could also be fabricated without the use of 3D scaffolds to confine the cell populations. It has also been shown that this method has promising use in stem cell transplantation by co-culturing hMSCs with fbs and inducing adipocyte differentiation while in a 3D multi-layered tissue-like structure.

The present application therefore includes a method for promoting the adhesion of cells comprising:
(a) contacting a first cell population with a liposome of type A under conditions for the fusion of the liposome of type A with the first cell population;
(b) contacting a second cell population with a liposome of type B under conditions for the fusion of the liposome of type B with the second cell population; and
(c) contacting the fused first cell population with the fused second cell population, wherein the liposomes of type A comprise a reactive functional group that reacts with a reactive functional group comprised in the liposomes of type B to form a chemical interaction that results in the adhesion of the first and second cell populations.

To promote the fusion of the liposomes to cells, a mixture of neutral, positively and/or negatively charged liposome-forming amphiphatic molecules may be used. For example, fusion to mammalian cells types, whose membranes comprise a negative charge, is promoted by incorporating positively charged lipids in to the liposome. While not wishing to be limited by theory, the positively charged lipid enhances membrane fusion via electrostatic destabilization. In an embodiment, the positively charged liposomes are incorporated in an amount of 1 mol % to about 5 mol %, or about 2 mol %. Promotion of liposome fusion to other cell types, including plants, bacteria, viruses and the like, can be done using a similar strategy depending on the characteristics of the cell membrane.

The conditions for the fusion of the liposomes with the cell populations generally involve adding an aqueous buffered solution of the liposomes to the cells in culture and incubating the cells in the presence of the liposomes for example, for 6 to about 24 hours. In an embodiment, the solution of the liposomes is added at a concentration of about 0.5 to 5 mM and about 1 to about 10 mL of this solution is added to about 1 to about 10 mL of the cultured cells. When the cell populations are incubated with the liposomes comprising a reactive functional group, membrane fusion occurs, resulting in the presentation of the reactive functional groups from the cell surfaces. These reactive functional groups are available for further reaction so that when these cell populations are contacted together, interconnected, 3D tissue-like structures form, mediated through chemoselective reactions between the complementary functional groups.

The contacting the fused first cell population with the fused second cell population can be done using any suitable means. For example, the cell populations may be combined in solution. As a representative example, oxyamine presenting rat2 fibroblasts were combined in solution with ketone-presenting Swiss albino 3T3 fibroblasts and, upon mixing, these two cell populations formed clusters and tissue-like masses. This is a significant finding as current methods to generate these types of structures require the support of a 3D hydrogen matrix and/or assisted assembly through an external stimulus.

Alternatively, one of the cell populations may be grown on a substrate and the second cell population added as a layer on top of the first population, followed by addition of alternate layers of the first and second population of cells. In this embodiment, larger, dense 3D tissue-like networks are formed with geometric control. In this embodiment, the 3D-tissue like networks are released from the substrate using, for example, agitation or washing, accordingly, this method provides the possibility for applications in tissue engineering and cellular transplantation.

Another alternative is to combine the two cell populations in a continuous fashion, for example, by flowing one stream comprising the first population of cells into a second stream comprising the second population of cells.

In an embodiment, at least one of the cell populations is a stem cell population and adhesion of a second population of a specific cell type results in induced differentiation and proliferation of the stem cells as the second cell type. This result holds great potential for areas of regenerative medicine and stem cell transplantation.

In a further embodiment of the application, the liposomes of type A and/or B further comprise biologically active agents, such as nucleic acids, proteins, peptides, small molecule drugs, carbohydrates and the like, and mixtures thereof, and fusion of the liposomes with the cell population results in the delivery of the biological agents into the cells. The biologically active agents may be entrapped within the liposome or may be incorporated into the liposome membrane.

In yet another embodiment, the liposomes of type A and/or B further comprise other functional molecules, such as fluorescent molecules, dyes and/or other indicator molecules, so that when the first and second cell populations are adhered, a physical or sensory change, such as a change in color or fluorescence occurs. These functional molecules may be entrapped within the liposomes or be incorporated into the liposome-forming amphiphatic molecules.

In another embodiment of the application, the liposomes of type A and type B further comprise fluorescent reporter molecules. In one embodiment, the fluorescent reporter molecules are incorporated into the liposome-forming amphiphatic molecules. When present in the liposome-forming amphiphatic molecules, it is an embodiment that these molecules are incorporated into the liposomes in an amount of about 0.5 mol % to about 5 mol %, or about 2 mol %. As a representative example, the fluorescent phospholipids, egg 1,2-diphytanoyl-sn-glycero-3-phosphoethanolamine-N-(7-nitro-2-1,3-benzoxadiazol-4-yl) (ammonium salt) (NBD-PE), and egg 1,2-dipalmitoyl-sn-glycero-3-phosphoethanolamine-N-(lissamine rhodamine B sulfonyl) (ammonium salt) (Rhod-PE), are used. The incorporation of fluorescent reporter molecules into the liposome-forming amphiphatic molecules allows for easy monitoring of liposome fusion and subsequent cell adhesion.

In a further embodiment of the application, the liposomes of type A and/or B further comprise biologically active agents, such as nucleic acids, proteins, peptides, small molecule drugs, carbohydrates and the like, and mixtures thereof, and fusion of the liposomes with the cell population results in the delivery of the biological agents into the cells. The biologically active agents may be entrapped within the liposome or may be incorporated into the liposome membrane.

The present application also includes cell populations whose surfaces have been modified with reactive functional groups by fusion with the liposomes of type A and/or B, compositions comprising these cell populations and all uses thereof.

The following non-limiting examples are illustrative of the present application:

EXAMPLES

Materials and Methods

All chemical reagents were of analytical grade and used without further purification. Lipids, egg palmitoyl-oleoyl phosphatidylcholine (POPC), egg 1-palmitoyl-2-oleoyl-phosphatidylglycerol (POPG), 1,2-dioleoyl-3-trimethylammonium-propane (DOTAP), egg 1,2-diphytanoyl-sn-glycero-3-phosphoethanolamine-N-(7-nitro-2-1,3-benzoxadiazol-4-yl) (ammonium salt) (NBD-PE), and egg 1,2-dipalmitoyl-sn-glycero-3-phosphoethanolamine-N-(lissamine rhodamine B sulfonyl) (ammonium salt) (Rhod-PE) were purchased from Avanti Polar Lipids (Alabaster, Ala.). Antibodies and fluorescent dyes were obtained from Invitrogen (Carlsbad, Calif.). FITC-labeled beads were purchased from Spherotech, Inc. (Forest Lake, Ill.) and all other chemicals were obtained from Sigma-Aldrich or Fisher. Swiss 3T3 albino mouse fibroblasts (fbs) were obtained from the Tissue Culture Facility at the University of North Carolina (UNC).

Transmission electron microscopy (TEM) images were acquired using a TF30He Polara G2 (FEI company) electron cryo microscope, operating at 300 keV. Images were recorded using a Tietz single port model 415 4k×4k CCD camera with a 15-µm pixel size. Fluorescence resonance energy transfer measurements (FRET) were performed using a SPEX Fluorolog-3 Research T-format Spectrofluorometer with an excitation wavelength of 471 nm. Dynamic light scattering was performed using a Nikomp model 200-laser particle sizer with a 5 mW HeNe laser at an excitation wavelength of 632.8 nm and using a Wyatt DynoPro plate reader. Flow cytometry was performed using a Dako CyAn ADP (Beckman-Coulter, Brea, Calif.), and the data were analyzed with Summit 4.3 software. Phase contrast and fluorescent imaging was performed and processed using a Nikon TE2000-E inverted microscope and Metamorph software, respectively.

Tetra(ethylene glycol)-terminated alkanethiol ($EG_4$) was synthesized as previously reported.[44] Fluorescein-ketone (7) was synthesized as previously reported.[45] The syntheses of O-dodceyloxyamine (A) (Scheme 1) and rhod-oxyamine (8) are described below.

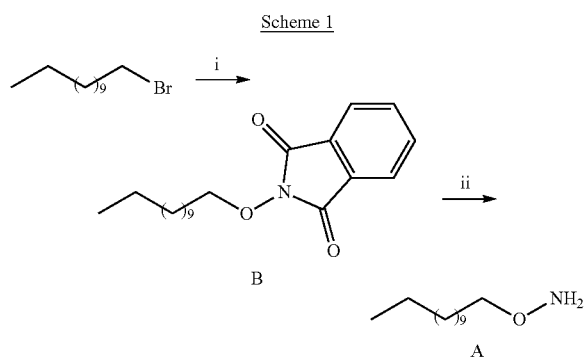

Scheme 1

Reagents and conditions. (i) N-hydroxyphthalimide (1.5 eq), NaHCO3 (1.5 eq), DMF, reflux, 80° C., 12 h; 87% and (ii) hydrazine (6 eq), dry DCM, N2, 12 h; 74%.

Example 1

2-(dodecyloxy)isoindoline-1,3-dione (B)

As shown in Scheme 1, 1-bromododecane was added to a solution of N-hydroxyphthalimide (1.96 g, 12.04 mmol, 1.5 eq) and sodium bicarbonate (10.11 g, 12.04 mmol, 1.5 eq) in DMF (20 mL) at 80° C. (1.93 mL, 8.02 mmol). The mixture was refluxed and stirred for 12 h. The reaction was diluted with DCM and washed with $H_2O$ (6×50 mL), 1 M $NaHCO_3$ (3×50 mL), and $H_2O$ (2×50 mL), dried over $MgSO_4$, and concentrated to afford a white solid, B (2.66 g, 87%). $^1$H NMR (400 MHz, $CDCl_3$) δ 0.91 (m, 3H), 1.28 (bm, 16H), 1.47-1.49 (m, J=9.2 Hz, 2H), 1.77-1.83 (m, J=22.0 Hz, 2H), 4.20-4.23 (t, J=13.6 Hz, 2H), 7.28-7.30, 7.75-7.77 (dm, J=4.8, Hz, J=5.6 Hz, 2H, 2H). (ESI) (m/z) [M+H$^+$]: 332.28.

Example 2

O-dodecyloxyamine (A)

As shown in Scheme 1, hydrazine was slowly added to a solution of B (2.65 g, 8.00 mmol) in dry DCM (30 mL) under inert atmosphere (Ar) (1.53 mL, 48.00 mmol, 6 eq). Upon addition, a white precipitate immediately formed. The mixture was stirred for 12 h. The reaction was diluted with DCM and washed with $H_2O$ (6×50 mL), dried over $MgSO_4$, and concentrated to afford a pale yellow oil, A (1.18 g, 74%). $^1$H NMR (400 MHz, $CDCl_3$) δ 0.88-0.91 (t, J=13.6 Hz, 3H), 1.28 (s, 18H), 1.57-1.60 (m, J=14.0 Hz, 2H), 3.65-3.69 (t, J=13.2 Hz, 2H). (ESI) (m/z) [M+H$^+$]: 201.22.

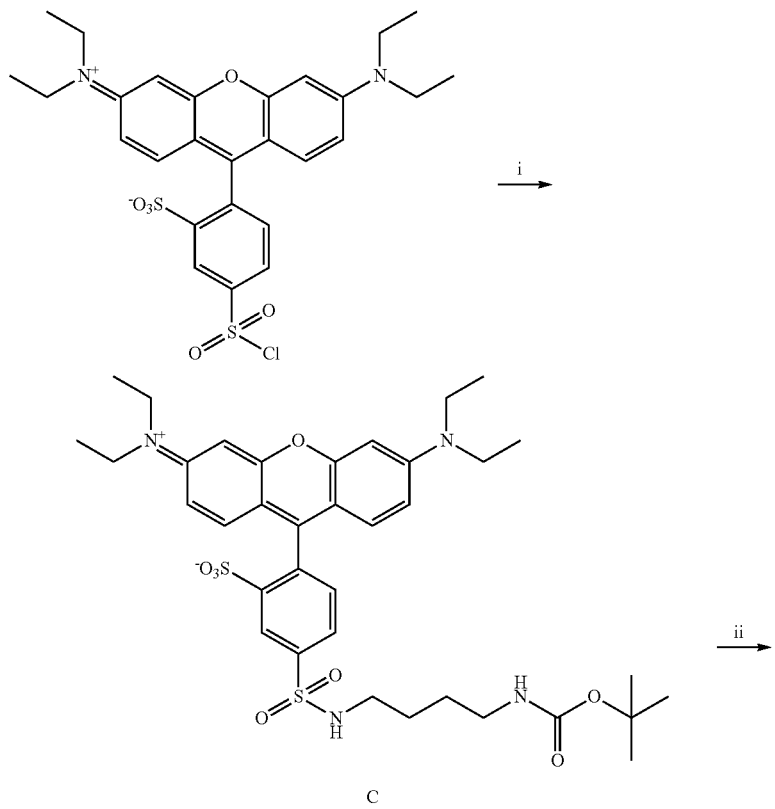

Scheme 2

-continued
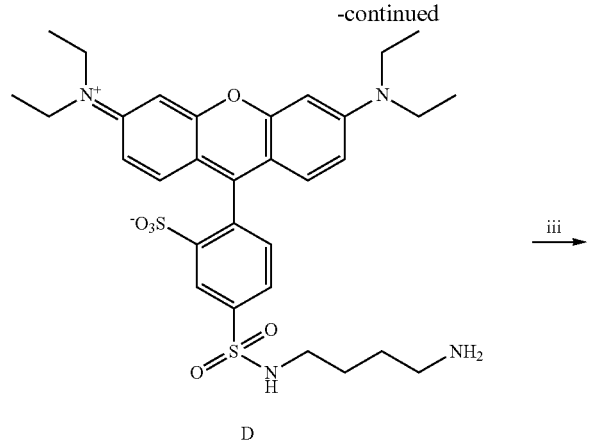
D
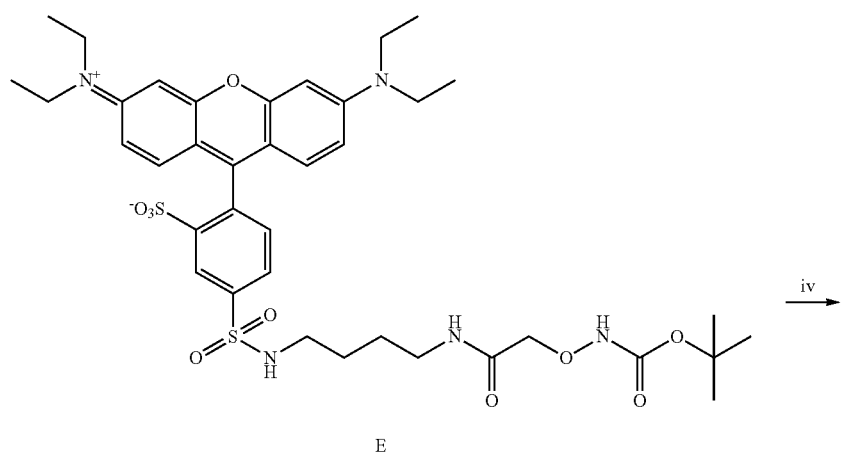
E
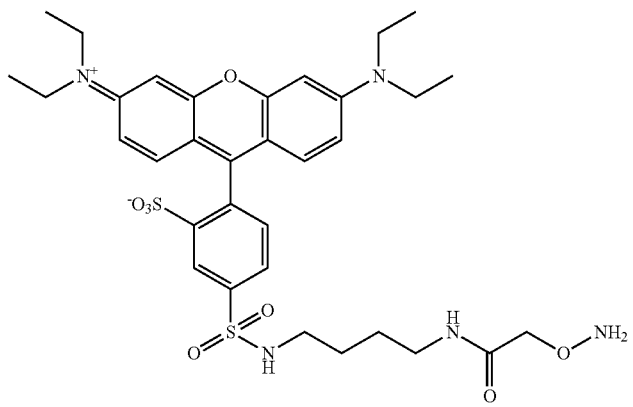
8
Reagents and conditions. (i) N-BOC-1,4-diaminobutane (1.5 eq), TEA (1.5 eq), CHCl₃, N₂, 25° C., 8 h; 95%, (ii) triisopropylsilane (TIPS)/H₂O/TFA (2.5:2.5:95), N₂, 25° C., 3 h; 85%, (iii) N-hydroxysuccinimide (NHS, 2 eq), N,N'-dicyclohexylcarbodiimide (DCC, 2 eq), aminooxy acetic acid (2 eq), TEA (excess), DMF, N₂, 25° C., 4 h; 60%, and (iv) TIPS/H₂O/TFA (2.5:2.5:95), N₂, 25° C., 3 h; 81%.

Example 3

(N-(4-(tert-butoxycarbonylamino)butyl)sulfamoyl)-2-(6-(diethylamino)-3-(diethylimino)-3H-xanthen-9-yl)benzenesulfonate (C)

As shown in Scheme 2, to a solution of rhodamine lissamine (0.880 g, 1.53 mmol) in chloroform ($CHCl_3$, 30 mL) at room temperature (RT) was added N—BOC-1,4-diaminobutane (0.431 g, 2.29 mmol, 1.5 eq) and TEA (0.305 mL, 2.29, 1.5 eq). The mixture was stirred for 8 h and then extracted with $H_2O$ (6×25 mL). The organic layers were concentrated to afford a dark purple solid C. $^1H$ NMR was taken in $CDCl_3$ to confirm C (1.045 g, 95%). TLC conditions for entire synthesis: $CHCl_3$:MeOH (7.5:2.5). $^1H$ NMR (400 MHz, MeOD) δ 1.09-1.07 (t, J=8.1 Hz, 6H), 1.36-1.33 (m, J=12.3, 15H), 1.66-1.64 (m, J=8.6 Hz, 4H), 3.47-3.44 (m, J=12.1, 6H), 4.20-4.18 (q, J=7.8 Hz, 4H), 5.66 (s, 1H), 5.77 (d, 1H), 6.01 (d, 1H), 6.34-6.30 (m, J=16.1 Hz, 2H), 7.21 (d, 1H), 7.29 (d, 1H), 7.98 (d, 1H), 8.04 (d, 1H). (ESI) (m/z) [M+H$^+$]: 716.31.

Example 4

5-(N-(4-aminobutyl)sulfamoyl)-2-(6-(diethylamino)-3-(diethyliminio)-3H-xanthen-9-yl)benzenesulfonate (D)

As shown in Scheme 2, to C (0.600 g, 0.837 mmol) was added a solution of TFA, $H_2O$, and triisopropylsilane (TIPS) in a ratio of 95: 2.5: 2.5 (10 mL). The mixture was stirred at RT under $N_2$ for 3 h and was then extracted with $CHCl_3$ and $H_2O$ (4×25 mL). The organic layers were dried and concentrated to afford a purple solid, D (0.45 g, 85%). $^1H$ NMR (400 MHz, MeOD) δ 1.11-1.09 (t, J=8.7, 6H), 1.33-1.31 (m, J=7.4 Hz, 6H), 1.70-1.67 (m, 4H, J=12.5, 4H), 2.63-2.62 (m, J=4.6 Hz, 2H), 3.51-3.49 (m, J=8.7 Hz, 6H), 4.20-4.18 (q, J=7.8 Hz, 4H), 5.64 (s, 1H), 5.71 (d, 1H; Ar—H), 6.02 (d, 1H), 6.32-6.30 (m, J=8.3 Hz, 2H), 7.24 (d, 1H), 7.30 (d, 1H), 7.98 (d, 1H), 8.04 (d, 1H). (ESI) (m/z) [M+H$^+$]: 628.27.

Example 5

2-(6-(diethylamino)-3-(diethyliminio)-3H-xanthen-9-yl)-5-(N-(2,2-dimethyl-4,8-dioxo-3,6-dioxa-5,9-diazamidecan-13-yl)sulfamoyl)benzenesulfonate (E)

As shown in Scheme 2, to a solution containing N,N'-dicyclohexylcarbodiimide (DCC, 0.394 g, 1.91 mmol, 2 eq), N-hydroxysuccinimide (NHS, 0.220 g, 1.91 mmol 2 eq), and aminooxy acetic acid (0.356 g, 1.91 mmol, 2 eq) in DMF was stirred under $N_2$ for 0.5 h. D (0.43 g, 0.684 mmol) was then added in DMF (20 mL), followed by TEA (excess). The mixture was stirred for 4 h and then concentrated. Flash chromatography was performed using $CHCl_3$:MeOH (8:2) to elute, E. The product was concentrated to afford a purple solid E (0.32 g, 60%). $^1H$ NMR (400 MHz, MeOD) δ 1.10-1.08 (t, J=8.8, 6H), 1.39-1.36 (m, J=12.3 Hz, 15H), 1.65-1.63 (m, J=7.9, 4H), 3.08-3.06 (m, J=8.0, 2H), 3.48-3.46 (m, J=8.3, 6H), 4.17-4.15 (q, J=7.7, 4H), 4.38 (s, 2H), 5.61 (s, 1H), 5.73 (d, 1H), 6.02 (d, 1H), 6.31-6.30 (m, J=4.4, 2H), 7.24 (d, 1H), 7.32 (d, 1H), 7.96 (d, 1H), 8.09 (d, 1H). (ESI) (m/z) [M+H$^+$]: 801.31.

Example 6

5-(N-(4-(2-(aminooxy)acetamido)butyl)sulfamoyl)-2-(6-(diethylamino)-3-(diethyliminio)-3H-xanthen-9-yl)benzenesulfonate (rhod-oxyamine, 8)

As shown in Scheme 2, to E (0.30 g, 0.374 mmol) was added a solution of TFA, $H_2O$, and triisopropylsilane (TIPS) in a ratio of 95: 2.5: 2.5 (10 mL). The mixture was stirred at RT under $N_2$ for 3 h and was then extracted with $CHCl_3$ and $H_2O$ (4×25 mL). The organic layers were dried and concentrated to afford a purple solid and flash chromatography was performed using $CHCl_3$:MeOH (8:2) to elute, 8 (0.21 g, 81%) $^1H$ NMR (400 MHz, $CDCl_3$) δ 1.12-1.00 (t, J=8.2, 6H), 1.42-1.40 (m, J=7.9, 6H), 1.62-1.60 (m, J=7.7, 4H), 3.07-3.05 (m, J=8.0, 2H), 3.45-3.42 (m, J=12.4, 6H), 4.11-4.09 (q, J=8.4, 4H), 4.24 (s, 2H), 5.64 (s, 1H), 5.75 (d, 1H), 6.02 (d, 1H), 6.29-6.27 (m, J=4; 2H), 7.28 (d, 1H), 7.31 (d, 1H), 7.92 (d, 1H), 8.05 (d, 1H). (ESI) (m/z) [M+H$^+$]: 701.28.

Example 7

Formation of Lipid Vesicles. Liposome Fusion Studies

Dodecanone (55 μL, 10 mM in $CHCl_3$ at 5 mol %) was dissolved with egg palmitoyl-oleoyl phosphatidylcholine (POPC) (430 μL, 10 mg/mL in $CHCl_3$, at 95 mol %) and O-dodecyloxyamine (60 μL, 10 mM in $CHCl_3$ at 5 mol %) was mixed with POPC (410 μL, 10 mg/mL in $CHCl_3$ at 75 mol %), and egg 1-palmitoyl-2-oleoyl-phosphatidylglycerol (POPG) (92 μL, 10 mg/mL in $CHCl_3$ at 20 mol %). Both lipid sample mixtures were then concentrated under high vacuum for 4 h. The dried lipid samples were reconstituted and brought to a final volume of 3 mL in PBS buffer, pH 7.4. The contents of the vial were warmed to 50° C. and sonicated for 20 min, in a tip sonicator, until the solution became clear and large unilamellar vesicles (LUVs) containing ketone (keto-LUV, 1) or oxyamine (oxy-LUV, 2) groups were formed (see FIG. 1b).

Example 8

FRET Fusion Studies

NBD-PE and rhod-PE were added to two separate vials at 2 mol %. The dried lipid samples were then reconstituted in 2.43 mL of PBS buffer, pH 7.4. The contents of the vial were warmed to 50° C. and sonicated for 20 min, in a tip sonicator, until the solution became clear, and LUVs containing ketone (keto-NBD-PE LUVs, 3) or oxyamine (oxy-rhod-PE LUVs, 4) groups were formed (see FIG. 1c).

Example 9

Liposome Fusion to Cells

To generate ketone- and oxyamine-containing liposomes for cell fusion studies, dodecanone (55 μL, 10 mM solution in $CHCl_3$ at 5 mol %) or O-dododecyloxyamine (60 μL, 10 mM solution in $CHCl_3$ at 5 mol %) were dissolved with egg-POPC (424 μL, 10 mg/mL in $CHCl_3$ at 93 mol %) and 1,2-dioleoyl-3-trimethylammonium-propane (DOTAP, 10 μL, 10 mg/mL in $CHCl_3$ at 2 mol %) in chloroform followed by concentration under high vacuum for 4 h. The dried lipid samples were then reconstituted and brought to a final volume of 3 mL in PBS buffer, pH 7.4. The contents of the vial were warmed to 50° C. and sonicated for 20 min, in a tip sonicator, until the solution became clear, and LUVs containing ketone (5) or oxyamine (6) groups were formed (FIG. 1d).

Example 10

Matrix-Assisted Laser-Desorption/Ionization Mass Spectrometry (MALDI-MS). Preparation of Gold-Coated MALDI Sample Plates Gold-coated MALDI sample plates (123×81 mm) (Applied Biosystems, Foster City, Calif.) were prepared by electron-beam deposition (Thermionics Laboratory Inc, Hayward, Calif.) of titanium (5 nm) and then gold (12 nm). In order to form self-assembled monolayers (SAM) of alkanethiolates on the plates, the slides were immersed in a 1-mM solution of aminooxyundecanethiol in EtOH for approximately 1 min, rinsed with EtOH and dried, and then backfilled with a 1-mM solution of mercaptoundecanol in EtOH for 1 h. Once removed from solution, the surfaces were rinsed with EtOH and dried before use.

Keto-LUVs (1) were generated as described above and were then delivered and allowed to react with the oxyamine-terminated MALDI sample plate (90 min). The plates were then washed with water (3×3 mL) and EtOH (2×3 mL) and dried before use.

MS analyses were carried out using an AB SCIEX TOF/TOF™ 5800 System (Applied Biosystems, Foster City, Calif.) (see FIG. 2a).

Example 11

Dynamic Light Scattering (DLS)

Keto- (1) and oxyamine- (2) LUVs were generated as described above and tested by DLS for monodispersity and uniformity. Light scattering experiments were performed using a Nikomp Model 200 Laser Particle Sizer with a 5 mW Helium-Neon Laser at an exciting wavelength of 632.8 nm. Standard deviation determinations were made using Gaussian analysis. A Wyatt DynoPro Dynamic Scattering Plate Reader was used to collect the light scattering data.

Example 12

FRET Analyses

Keto- (3) and oxyamine- (4) LUVs containing NBD-PE and rhod-PE, respectively, were generated as described above and tested by FRET. All fluorescence measurements were performed in a SPEX Fluorolog-3 Research T-format Spectrofluorometer. NBD fluorescence was measured at 471 nm (excitation) and 531 nm (emission), maintaining narrow excitation slits to reduce light scattering interference. To obtain FRET measurements, the NBD dye was excited at 471 nm, and the emission was scanned through 600 nm, and the emission signal for rhod-PE was observed at 578 nm. Fluorescence was followed immediately after mixing oxy-rhod-PE LUV (4, 3 mM in PBS, 100 μL) with keto-NBD-PE LUV (3, 3 mM in PBS, 100 μL) for approximately 2 h at 2 min intervals. The total lipid concentrations were adjusted to 0.2 mM, and the two LUV populations were had a 1:1 molar ratio. A constant flow of water was passed through the cuvette holder for temperature control. The temperature was maintained at 25° C. (see FIG. 2c).

Example 13

TEM Analyses

Keto- (1) and oxyamine- (2) LUVs were made as described above (0.2 mM in PBS, pH 7.4). The two vesicle solutions (1:1) were mixed at room temperature for 30 min. 4 μL of vesicles suspended in buffer were applied to standard lacey carbon EM grids which were prepared according to published methods. The specimens were blotted from behind and then submerged into aurenyl acetate solution for staining. The hydrated specimens were then placed into a TF30He Polara G2 (FEI company) electron cryo microscope operating at 300 keV. Images were recorded using a Tietz single port model 415 4k×4k CCD camera with a 15 micron pixel size on the chip. Pixel sizes at the specimen level were used to calculate accurate dimensions for the specimen (see FIG. 2b).

Example 14

Fibroblast (Fb) Culture

Swiss 3T3 albino mouse fbs and Rat2 fbs were cultured in Dulbecco's Modified Eagle Medium (Gibco) containing 10% calf bovine serum (CBS) and 1% penicillin/streptomycin at 37° C. in 5% $CO_2$.

Cells were seeded onto a tissue culture plate and allowed to grow for 48 h at 37° C. in 5% $CO_2$ in CBS media.

Example 15

Cell-Surface Engineering

Figure 3:
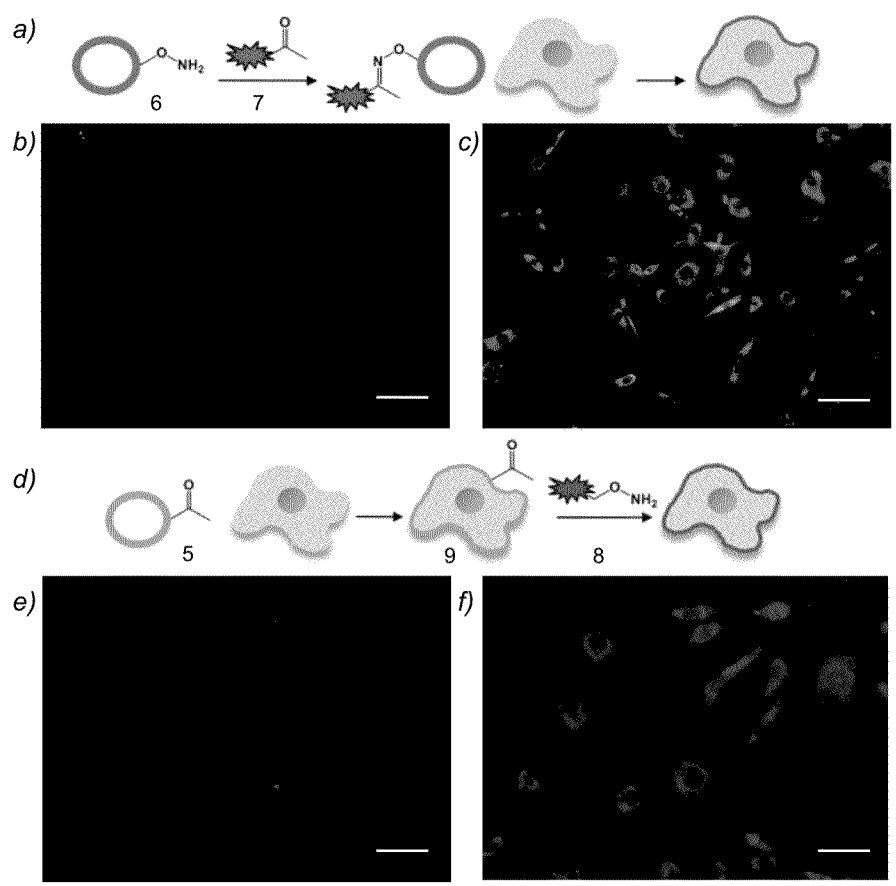
FIG. 3 (Top) shows a schematic describing the delivery and subsequent fusion of fluorescent liposomes to cell surfaces with corresponding brightfield and fluorescent images. (a) Oxy-LUVs (6, 3 mM) were reacted with fluorescein-ketone (7, 0.15 mM, 2 h) to generate green fluorescent liposomes. The fluorescent liposomes were then added to fibroblasts (fbs) in culture, resulting in the fluorescent labeling of cells after liposome fusion to the cell membrane. Micrographs show (b) control cells where liposomes not containing oxyamine groups were incubated with fluorescein-ketone and added to fbs in culture for 2 h and (c) green fluorescently labeled cells after oxyamine-functionalized liposomes were incubated with fluorescein-ketone and delivered to fbs (2 h).

Two cell-surface engineering methods were employed to fluorescently label fbs. In this first method, a solution of oxyamine vc-LUVs (6, 3 mM) was incubated with a ketone-functionalized fluorescein (7, 0.15 mM, 1 eq, 2 h), forming fluorescently labeled liposomes. The liposomes were then added to fbs in culture for 2 h. After fusion, the cells were washed with PBS (3×2 mL), trypsinized (1 mL, 5 min, 37° C., 5% $CO_2$), diluted with CBS-containing media (~$10^2$/mL), and seeded to a glass substrate (1×1 $cm^2$, 2 h). The cells were then imaged under a fluorescence microscope with an exposure time of $1/1200$ s. In the second method, a solution of keto-LUVs (5, 200 μL, 0.6 mM) was added to fbs in culture for 2 h, resulting in membrane fusion and subsequent display of ketones from the cell surface (9). Rhod-oxyamine (8, 100 μL, 0.7 mM in $H_2O$) was then added the cells for 2 h. After oxime formation, the fbs were washed with PBS (3×2 mL), trypsinized (1 mL, 5 min, 37° C., 5% $CO_2$), diluted with CBS-containing media (~$10^2$/mL), and seeded to a glass substrate (1×1 $cm^2$, 2 h). The cells were then imaged under a fluorescence microscope with an exposure time of $1/1200$ s (see FIG. 3).

Example 16

Cell Adhesion Patterning

Figure 4:
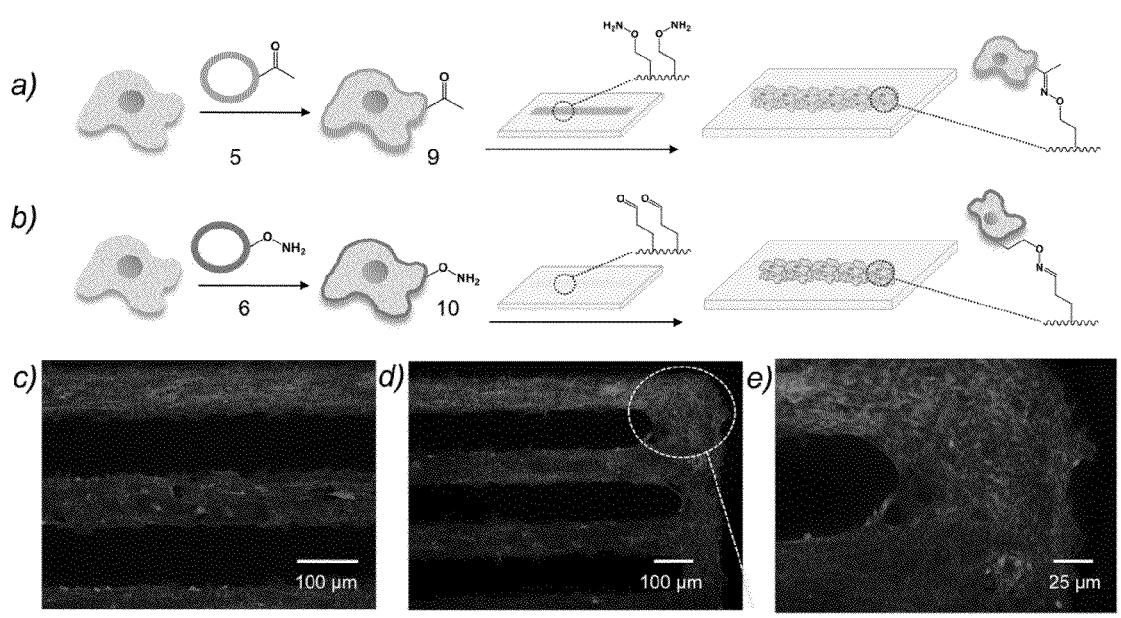
FIG. 4 shows schematics and fluorescent micrographs of rewired cells adhered to patterned self-assembled monolayers (SAMs) of alkanethiolates on gold substrates. (a and b) Keto- (5) and oxyamine-LUVs (6, 3 mM, 4 h) were cultured with separate fb populations, producing ketone- and oxyamine-presenting fbs (9 and 10, respectively). These cells were then seeded (~$10^2$ per mL, 2 h) to patterned, oxyamine- and aldehyde-terminated SAMs (10%), respectively, and allowed to adhere through stable oxime conjugation. The unpatterned surface regions present tetra(ethylene glycol), which resists cell and protein adsorption. The cells then grew and proliferated only filling out the oxyamine- and aldehyde-tethered surface regions, respectively. (c) A fluorescent micrograph of patterned ketone-fbs (9), adhered to an oxyamine-terminated SAM is shown. (d and e) Fluorescent micrographs of patterned oxyamine-fbs (10), adhered to an aldehyde-terminated SAM are demonstrated. Cells were stained with DAPI (nucleus) and phalloidin (actin).

Self-assembled monolayers (SAMs) presenting aldehyde or oxyamine and tetra(ethylene glycol) ($EG_4$) groups were patterned using microfluidic oxidation and microfluidic lithography, respectively.[34,35] $EG_4$ has been shown to passivate substrates against cell and protein adsorption.[36] Therefore, the ratio of $EG_4$ and aldehyde or oxyamine groups was 90:10 to ensure that fbs were only adhering to the patterned surface regions that presented 10 oxyamine or aldehyde groups, driven via oxime conjugation. Fbs were separately cultured with keto- (5) or oxyamine- (6) LUVs as previously described and were then seeded (~$10^2$ cells/mL, 2 h) to the patterned oxyamine or aldehyde surfaces, respectively. Media that 10% calf bovine serum (CBS) and 1 penicillin/streptomycin was then added, and the substrates were incubated at 37° C. in 5% $CO_2$ for 4 d. Cells cultured with liposomes, not containing the key functional groups, did not attach to the patterned surfaces. Substrates were then stained and imaged by fluorescence microscopy. An exposure time of 400 and 1200 ms were used to image nuclei and actin, respectively (see FIG. 4).

Example 17

Flow Cytometry

Figure 5:
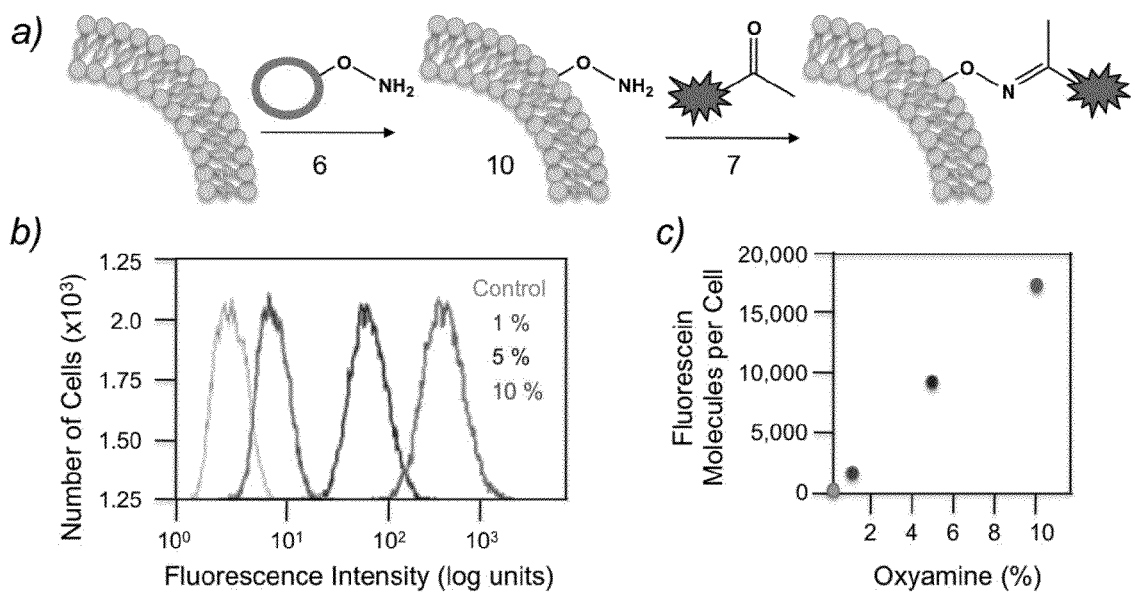
FIG. 5 shows cell surface molecule quantification using flow cytometry. (a) Oxyamine-LUVs (6, 3 mM) were added to fbs in culture (4 h), resulting in membrane fusion and subsequent display of oxyamine groups from cell surfaces (10). Ketone-functionalized fluorescein (7, 0.15 mM 2 h) was then reacted with the fbs, generating fluorescently labeled cells. (b) Liposomes with varying oxyamine mol % (0%, 1%, 5%, and 10%) were generated and cultured with separate populations of fbs. After reacting with ketone-fluorescein, the cell populations were washed with PBS, trypsinized, centrifuged, resuspended in RPMI media, and tested using FACS analyses. As shown, the fluorescence intensity increased with increasing oxyamine concentration. (c) The number of molecules present at the cell surface with respect to oxyamine concentration was quantified using flow cytometry. A bead with a known FITC molecule density was employed as a standard comparison to calculate the number of oxyamines after oxy-LUVs (6) with 0%, 1%, 5%, and 10% oxyamine was cultured with cells. As the oxyamine concentration increased, the molecules per cell increased linearly (0%, 128; 1%, 1600; 5%, 9800; and 10%, 17400). Twenty thousand cells were counted for each sampling.

Liposomes with varying oxyamine mol % (i.e., 0%, 1%, 5%, and 10%) were generated and cultured with separate populations of fbs (6, 3 mM, 4 h), resulting in membrane fusion and subsequent display of oxyamine groups from cell surfaces (10). Ketone-functionalized fluorescein (7, 0.15 mM 2 h) was then reacted with the fbs, generating fluorescently labeled cells. The control cells (i.e., not displaying oxyamine groups) were incubated with ketone-fluorescein for 2 h each, under the same conditions. The cells were then washed with PBS (3×5 mL), trypsinized (1 mL, 5 min, 37° C., 5% $CO_2$), centrifuged (5 min, 1000 rpm), resuspended in RPMI (without phenol red), centrifuged (5 min, 1000 rpm), and resuspended in RPMI (~$10^7$ cells/2 mL). Fluorescence-assisted cell sorting analyses (FACS) of the control and fbs with 1%, 5%, and 10% oxyamine were then performed (2×$10^3$ cells). Fluorescence measurements were calibrated using RCP-5-30 beads (~$10^7$ beads/mL, 2×$10^3$ beads counted, Spherotech, Inc., Lake Forest, Ill.) of known fluorescein equivalent molecule density.[37] The RCP-5-30 beads contain a mixture of several similar size particles with different fluorescence intensities and a blank. Every particle contains a mixture of fluorophores that allows excitation at any wavelength from 365 to 650 nm. As a result, the RCP-30-5 beads have a two-fold purpose: (1) calibrate the different channels in the flow cytometer being used and (2) cross-calibrate the relative number of fluorophores with cells or particles stained with known number of spectral matching fluorophores, such as FITC, to estimate the number of fluorophores on stained cells. No background is required to be subtracted because the different fluorophores are calibrated to the different flow cytometer channels. The raw data obtained in FIG. 5(b) were cross-calibrated to the calibration curve that is generated with the RCP-30-5 beads to obtain the values seen in FIG. 5(c). The approximations of FITC molecules per cell in FIG. 5(c) were determined by cross calibrating the 0% (control), 1%, 5%, and 10% oxyamine-containing liposomes to the standard curve (blank and 5 fluorophores) generated using the manufacturer's excel spreadsheet and instructions (Spherotech, Inc., Lake Forest, Ill.). After generating a standard calibration curve with the RCP-30-5 beads, the mean fluorescence intensities obtained from the FITC channel, were cross calibrated with the curve using the manufacturer's spreadsheet to produce an approximation of the number of molecules per cell. The number of counted beads and each sample were the same.

Fluorescent intensities based on number of cells counted were compared to the standard bead and control cells lacking fluorescent molecule conjugation and approximate numbers of fluorescent compound bound to the surface was calculated. Flow cytometry was carried out using a Dako CyAn ADP (Beckman-Coulter, Brea, Calif.), and data were analyzed with Summit 4.3 software.

Example 18

3D Spheroid Generation

Keto- (1) and oxyamine-LUVs (2) were added to two separate fb populations in culture for (3 mM in tris buffer, 400 μL added to 4 mL, 12 h), resulting in fusion and display of ketones and oxyamines from the cell surface. Oxyamine-presenting Rat2 fbs (10) contained an m-cherry label (nucleus) for enhanced visualization, while the ketone-presenting Swiss 3T3 albino mouse fb (9) contained no fluorescent label. These two cell populations were then trypsinized and mixed together (~$20^4$ cells/mL, 4 mL total) in serum containing (10% CBS, pH of 7.4) media in a 10 mL-flask and incubated at 37° C. and 5% $CO_2$ for 3 h. After mixing, the cells were seeded on a glass surface (~$20^4$ cells/mL, 1 mL) and visualized under a Nikon TE2000-E inverted microscope or by scanning electron microscopy. Image acquisition and processing was performed using Metamorph software. An exposure time of 75 ms was used to image all spheroids.

Example 19

Scanning Electron Microscopy (SEM) of 3D Spheroids

Spheroids were assembled in solution (reaction for 3 h as described above), delivered to a glass slide (~$20^4$ cells/mL, 1 mL, 0.8×0.8 $cm^2$), and then fixed with 10% formalin in PBS for 15 min. The substrate was then washed with water (15 min), and cells were then dehydrated stepwise in 30, 50, 70, 90, and 100% ethanolic solutions for 15 min each. After critical point drying and sputtering 2 nm of gold, the sample was ready for imaging using a Hitachi S-4700 field emission scanning electron microscope (Hitachi High Technologies America, Inc., Schaumburg, Ill.).

Example 20

Human Mesenchymal Stem (hMSC) Cell Culture hMSCs and basic, growth, and differentiation media were obtained from Lonza (Basel, Switzerland). hMSCs were cultured in Dulbecco's Modified Eagle Medium (Gibco) containing 10% fetal bovine serum (FBS) and 1% penicillin/streptomycin at 37° C. in 5% $CO_2$. Culturing with induction medium as described in the Lonza protocol induced Adipogenic differentiation.

Example 21

Immunohistochemistry

After the growth of 3D tissue-like structures and co-culture with Swiss 3T3 albino mouse fb, surfaces were fixed with formaldehyde (4% in PBS, 30 min). Substrates were then immersed in a solution containing water and 60% isopropyl alcohol (3-5 min), followed by staining with Oil Red O (5 min) and Harris Hemotoxylin (1 min) (6,7). Substrates were visualized by phase contrast microscopy using a Nikon TE2000-E inverted microscope. Image acquisition and processing was performed using Metamorph software. An exposure time of 75 ms was used to image all HMSCs.

Example 22

Directed 3D Tissue-Like Multi-Layers

Ketone-functionalized fbs (9) were seeded (~$10^4$ cells/mL) to microcontact printed patterned (1 mM hexadecanethiol in EtOH, printed on gold 5 s, backfilled with 1 mM $EG_4$ in EtOH, 16 h) surfaces presenting fibronectin (10 mg/mL, 2 h) for 2 h. The cells were allowed to grow for 3 d (37° C. in 5% $CO_2$).[29] Oxyamine-functionalized fbs (10) (~$10^4$ cells/mL) were then seeded to surfaces for 2 h, followed by addition of serum-containing (10% CBS) media to promote cell growth. The cells were cultured for 3 more d before imaging. After generation, substrates were fixed, stained, and imaged by confocal microscopy as described below.

Example 23

Cell Staining for Imaging

Cells were fixed with formaldehyde (4% in PBS) and permeated (PBS containing 0.1% Triton X-100). A fluorescent dye mixture, containing phalloidin-TRITC (actin) and DAPI (nucleus) was then made in PBS containing 5° A) normal goat serum and 0.1% Triton X–100. Cells were incubated with the dye solution for 2 h. The substrates were then secured in fluorescence mounting medium (Dako, Carpinteria, Calif., USA), which enhances the visualization of cells when viewed under a fluorescent microscope on a glass cover slip. An exposure time of 400 and 1200 ms were used to image nuclei and actin, respectively.

Example 24

Confocal Microscopy

Cell clusters and tissue formation were visualized with a Nikon Eclipse TE2000-E inverted microscope (Nikon USA, Inc., Melville, N.Y.). The data were recorded using Leica software and a spectral confocal microscope (LeicaMicrosystems, Bannockburn, Ill.). An average of 84 image scans were used to generate the 3D reconstructions with Volocity software.

Example 25

3D Co-Culture Spheroid and Multi-Layer Generation. Spheroids

Keto- (1) and oxyamine LUVs (2) were generated as previously described and were added to hMSCs and fbs (3 mM in tris buffer, 400 µL added to 4 mL, 12 h), respectively, and were cultured, resulting in fusion and display of ketones and oxyamines from the cell surface. These two cell populations were then trypsinized and mixed together in serum containing (10% FBS, pH of 7.4) media in a 10 mL flask and incubated at 37° C. and 5% $CO_2$ for 1, 2, 3, and 5 h. After mixing for the allotted time, cells were seeded onto a glass surface and visualized under a Nikon TE2000-E inverted microscope under the brightfield setting (75 ms exposure time). Controls were also performed where hMSCs displaying ketone groups were co-cultured with fbs (not displaying oxyamine groups) for each of the corresponding time points, 1, 2, 3, and 5 h, seeded onto glass, and imaged under the brightfield setting (75 ms). Image acquisition and processing was performed using Metamorph software.

Example 26

Multi-Layers

Keto- (1) and oxyamine-LUVs (2) were added to hMSC and fbs (3 mM in tris buffer, 400 µL added to 4 mL, 12 h), respectively, and were cultured, resulting in fusion and display of ketones and oxyamines from the cell surface. hMSCs (7) displaying ketone groups were trypsinized and cultured on glass slides ($10^5$ cells/mL) and allowed to grow for 2 d. Fbs presenting oxyamines (10) were then trypsinized and added ($10^5$ cells/mL) to the hMSCs. These cells were co-cultured in media (10% FCS) for 3, 5, and 7 d, resulting in the formation of 3D multi-layered, tissue-like structures of hMSCs and fbs.

Example 27

Cell Viability Assay

Cell viability of 3D spheroid and multi-layered tissue-like structures was assessed using a trypan blue viability assay (Hyclone, Fisher Sci, Pittsburgh, Pa.). Fb spheroid and multi-layer structures were prepared as previously described. A solution of 0.4% trypan blue in PBS was made and diluted in CBS (1:1) containing the spheroids (1, 3, and 5 h after mixing, $20^4$ cells/mL) in solution and multi-layer cell sheets (3, 5, and 7 d after a second fb population was added, $10^5$ cells/mL) on a glass slide. Trypan blue was allowed to react with the cells for 2 min, at which time spheroids and surfaces were imaged and false colored with blue for enhanced visualization using a Nikon TE2000-E inverted microscope. As a control, cells were cultured for 7 d to generate a multilayer and were then fixed as mentioned above. Trypan blue was allowed to react for 2 min, and cells were imaged. For phase contrast and fluorescent imaging, exposure times of 75 and 400 ms were used, respectively.

Results and Discussion

An oxime ligation strategy was employed herein to generate a number of large unilamellar vesicles (LUVs) that present ketone or oxyamine functional groups. Liposome-liposome fusion events were first initiated through molecular recognition and subsequent oxime bond formation and the fusion was characterized using fluorescence resonance energy transfer (FRET), matrix-assisted laser-desorption/ionization mass spectrometry (MADLI-MS), dynamic light scattering (DLS), and transmission electron microscopy (TEM). Next, liposomes containing ketone and oxyamine groups were cultured with 3T3 Swiss albino fibroblasts, resulting in membrane fusion and display of oxyamines and ketones from the cell surface for further fluorescent probe conjugation. For the liposome-liposome fusion events studied by MALDI-MS (FIG. 2a), DLS (FIG. 2d), and TEM (FIG. 2b), dodecanone and dodecyloxyamine molecules were incorporated, separately, into neutral, egg palmitoyl-oleoyl phosphatidylcholine (POPC) at a ratio of 5:95 to form keto-LUVs (1) and oxyamine-LUVs (2), respectively (FIG. 1a and 1b). When observing liposome fusion via FRET analyses (FIG. 2c), dodecanone molecules were mixed with POPC and fluorescence donor, egg 1,2-diphytanoyl-sn-glycero-3-phosphoethanolamine-N-(7-nitro-2-1,3-benzoxadiazol-4-yl) (NBD-PE) at a ratio of 5:93:2 to form keto-NBD-PE-LUVs (3), while dodecyloxyamine molecules were incorporated into POPC, negatively charged, egg 1-palmitoyl-2-oleoylphosphatidylglycerol (POPG), and fluorescence acceptor, egg 1,2-dipalmitoyl-sn-glycero-3-phosphoethanolamine-N-(lissamine rhodamine B sulfonyl) (rhod-PE) at a ratio of 5:73:20:2 to form oxyamine-rhod-PE-LUVs (4). Finally, liposomes that contained dodecanone, POPC, and cationic lipid, 1,2-dioleoyl-3-trimethylammonium-propane (DOTAP) (5:93:2, 5) and liposomes that composed of dodecyloxyamine, POPC, and DOTAP (5:93:2, 6) were generated to investigate liposome-cell fusion processes (FIG. 1d). Cationic lipid, DOTAP, was incorporated to induce membrane fusion due to the electrostatic interactions with the negatively charged cell surface.[36,47]

Fusion methodology and DLS analyses. An embodiment of the general fusion methodology is described in FIG. 1a. Two liposome populations (1 & 2, 3 & 4, or 5 & 6) were mixed, resulting in liposome docking, adhesion, and finally fusion due to the formation of stable, interfacial oxime bonds. Depending on the application, liposomes fuse to each other, forming larger liposomal structures (FIG. 2b) or to cell surfaces and then be further conjugated with the corresponding oxime component. DLS was performed upon mixing liposomes 1 and 2 over 2 h to monitor vesicle size change as a function of time. Increases in vesicle size were observed due to aggregation, adhesion, or fusion (top trace, FIG. 2d). Liposome saturation was reached ~80 min after mixing. It is believed that in some cases, liposomes 1 and 2 associate with each other through oxime chemistry and initiate docking/adhesion until enough liposomes have clustered to induce a sharp growth in size. The ketone and oxyamine concentrations were initially varied and it was found through cell-surface engineering experiments and FACS analyses that the higher the ketone and oxyamine concentration led to increases of these functional groups on the cell surface. However, increasing the concentration of functional groups led to faster fusion events but did not necessarily increase the liposome size after liposome-liposome fusion. In control reactions, LUVs not presenting ketones were reacted with LUVs containing oxyamines (1) (bottom trace, FIG. 2d). Likewise, LUVs containing ketone groups (2) were mixed with LUVs that did not display oxyamines. For both of these control experiments, no size change was observed over time. This result strongly supports that liposome adhesion and fusion are driven by chemoselective oxime bond formation between the ketone- and oxyamine-alkanes.

Figure 2:
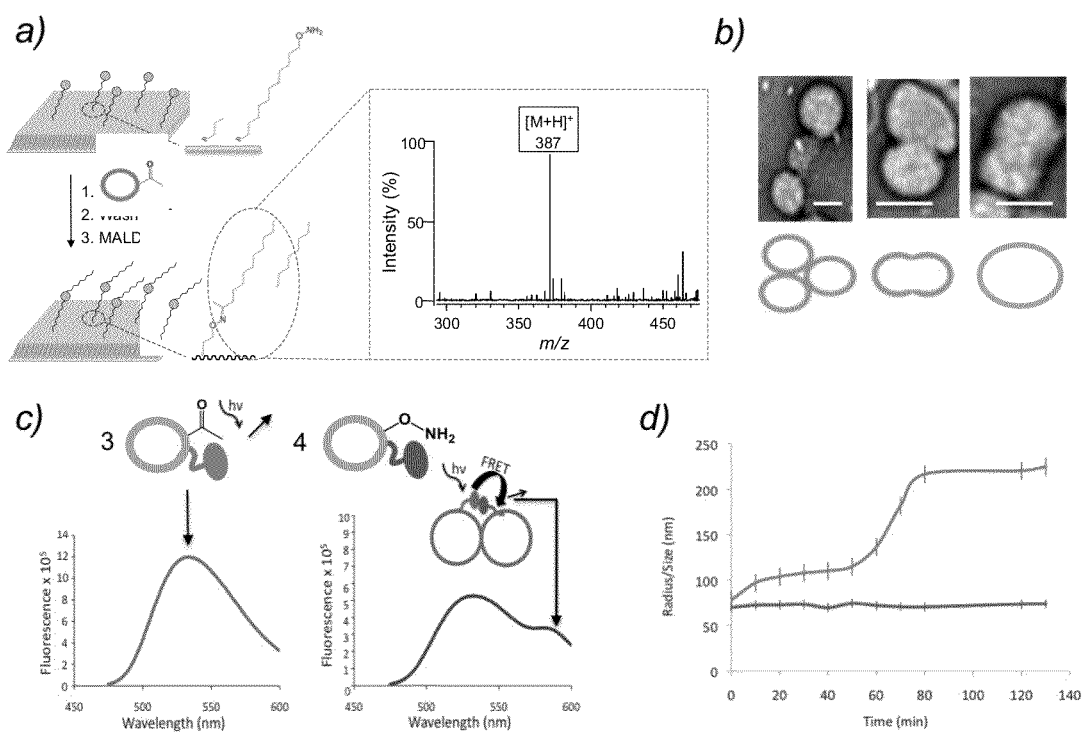
FIG. 2 shows the characterization of the formation of fused and adhered liposomes based on chemoselective oxime conjugation. (a) Mass spectrometry (MS) data representing the oxime ligation of keto-LUVs to self-assembled monolayers (SAMs) of oxyamine-terminated alkanethiol on a gold surface are displayed. Matrix-assisted laser desorption/ionization (MALDI) was performed after keto-LUVs were delivered to the surface, and a mass of 387 units was detected, confirming oxime conjugation. (b) Structural analyses using transmission electron microscopy (TEM), representing the adhesion and fusion of keto- (1) and oxyamine- (2) LUVs over time. The following images are shown from left to right: multi-adherent liposomes that are not fused; partially fused liposomes; and a single, large liposome after complete fusion. The scale bars represent 60 nm. (c) Fluorescence resonance energy transfer (FRET) analysis of liposome adhesion and fusion was monitored over 2 h. Fluorescence emission of keto-NBD-PE/PC LUVs (3), excited at 460 nm, was observed by scanning 475-600 nm (left-side trace). Fluorescence emission of keto-NBD-PE/PC LUVs (3) mixed with oxyamine-rhod-PE/PC/POPG LUVs (4) is represented (right-side trace). A new FRET emission peak is observed at 578 nm showing mixed liposome adhesion. (d) Dynamic light scattering (DLS) was performed upon mixing liposomes (1 and 2) to monitor vesicle size change as a function of time. Increases in vesicle size were observed due to aggregation, adhesion, or fusion (top trace). Liposome saturation was reached ~80 min after mixing. Without the presence of ketone and oxyamine functional groups, the LUV size remains constant (bottom trace).

TEM. Structural insight into the formation of different adhered and fused liposomes was observed through TEM (FIG. 2b). Vesicles of different sizes and shapes result after 2 h of liposome mixing (keto-LUV, 1 and oxyamine-LUV, 2). The liposome size gradually increases with time and is consistent with the data collected from other sizing experiments (e.g., DLS). Upon reaction, the following three structures were observed: multi-adherent liposomes that were not fused, partially fused liposomes, and completely fused, large uni- and multi-lamellar liposomes (FIG. 2b).

FRET. FIG. 2c shows a liposome fusion assay involving FRET characterization. A lipid-bound FRET pair, NBD-PE (donor) and rhod-PE (acceptor), were incorporated at 2 mol % concentration during liposome generation to produce keto-NBD-PE LUVs (3) and oxyamine-rhod-PE LUVs (4), respectively. Hypothetically, fusion of these vesicles should result in a gradual decrease in the donor emission peak and an increase in acceptor emission peak due to the close proximity of these dyes. As shown, vesicle mixing resulted in this FRET fusion signature. Fusion was observed immediately upon mixing 3 and 4, slowing within 2 h to a stable population, which is similar to earlier sizing results. An emission peak was not observed for the acceptor rhodamine dye when performing control experiments that tested the energy transfer with an LUV that did not contain oxyamines. Similar results were observed when LUVs that did not contain ketones or oxyamines were mixed. These data further support that liposome aggregation and fusion are based on chemoselective oxime bond formation.

MALDI-MS. Oxime conjugation, after keto-LUV (1) fusion, was confirmed by MALDI-MS analysis. Self-assembled monolayers (SAMs) of aminooxyundecanethiol were formed on a gold-coated, sample plate. A solution containing keto-LUVs (1) was then allowed to fuse and react with the surface for 90 min, followed by MALDI-MS examination. A mass of 387 units was detected, confirming successful oxime conjugation, resulting from liposome fusion on the surface (FIG. 2a).

Cell-surface labeling. In an embodiment of the present application, oxime chemistry is used to tailor and fluorescently label cell surfaces via a novel liposome fusion strategy. As mentioned, cationic lipid, DOTAP, was incorporated within keto- and oxyamine-LUVs to initiate electrostatic destabilization and subsequent fusion to the cell membrane. As such, the minimum DOTAP concentration required to facilitate liposome-cell fusion was determined to be 2 through fluorescence labeling optimization. Keto-LUVs were generated using DOTAP and POPC concentrations that ranged from 0.5% to 5% and 90% to 94.5%, respectively, while maintaining a 5-% ketone concentration. These liposomes were incubated with fibroblasts (fbs) for 4 h, conjugated with an oxyamine-tethered rhodamine (rhod-oxyamine, 8) (0.7 mM, 2 h), and the cell fluorescence intensities were then compared. From 2% to 5% DOTAP, the intensities were almost identical, indicating that 2% DOTAP is sufficient to initiate fusion. The liposomes for liposome-cell fusion events were approximately ~60 nm in diameter, similar to those used for the liposome-liposome fusion characterization.

Given this optimized lipid ratio (POPC/ketone or oxyamine/DOTAP at 93:5:2), two cell-surface engineering methods were employed to fluorescently label fbs. Similar to the optimization experiments, a solution of keto-LUVs (5, 200 μL, 0.6 mM) was added to fbs in culture for 2 h, resulting in membrane fusion and subsequent display of ketones from the cell surface (9) (FIG. 3d). Rhod-oxyamine (8, 100 μL, 0.7 mM in $H_2O$) was then added the cells for 2 h. After oxime formation, the fbs were washed with PBS, trypsinized, diluted with CBS-containing media (~$10^2$/mL), seeded to a glass substrate, and imaged under a fluorescent microscope. As observed in FIG. 3f, the conjugation of rhod-oxyamine with ketone-presenting fbs resulted in the fluorescence labeling of cells. When the control fbs (i.e., no ketone groups present) were reacted with rhod-oxyamine (8) and then imaged, no fluorescence was observed (FIG. 3e). Demonstrating the flexibility of this liposome-based surface labeling strategy, fb surfaces were modified to present a ketone-functionalized fluorescein dye (7) after oxyamine-LUV-ketone-fluorescein conjugation and subsequent membrane fusion (FIG. 3a). A solution of oxyamine-LUVs (6, 3 mM) was incubated with a ketone-functionalized fluorescein (7, 0.15 mM, 1 eq, 2 h), generating fluorescently labeled liposomes. The liposomes were then added to fbs in culture for 2 h. After fusion, the cells were washed with PBS, trypsinized, diluted with CBS-containing media (~$10^2$/mL), seeded to a glass substrate, and imaged under a fluorescent microscope. FIG. 3c presents fluorescently labeled fbs after fusion with fluorescein-functionalized LUVs. Through fluorescent and confocal imaging, it appears that after membrane fusion and/or endocytosis of cultured liposomes, fluorescence is also observed in several membrane organelles. This is an advantage of the system in that ketone or oxyamine groups are present at the cell surface and also decorate various internal membranes. It may be possible to label internal organelles with oxyamine chemistry for future targeting studies and applications. These lipids and fluorophores are likely packaged and trafficked to and from the cell surface and internal compartments. However, enough functional groups are present on the cell surface to provide handles for further oxime chemistry conjugation to tailor cell surfaces. When liposomes not containing oxyamine groups were incubated with fluorescein-ketone and added to fbs in culture for 2 h, no fluorescence was observed (FIG. 3b). Thus, control images indicated that reaction and labeling does not occur without the proper oxime recognition pair (FIGS. 3b and 3e). Furthermore, under these conditions, no changes were observed in cell behavior upon liposome fusion to cells, which is a very important feature for future in vivo applications. Thus, by combining liposome fusion and oxime chemistry, the cell surface was tailored with either ketone groups or oxyamine groups, which act as chemoselective cell-surface receptors for a range of small molecules, ligands, biomolecules, and nanoparticles.

Cell patterning: Rewiring adhesion. The ability to pattern and adhere cells to different materials, such as thin metal films, polymer scaffolds, and nanoparticles, with a simple and straightforward chemoselective and bio-orthogonal approach would be beneficial for cell biology, tissue engineering, and biotechnology. Thus, the liposome fusion was employed for cell-surface engineering to modify and rewire cell surface to adhere to patterned 2D substrates, directed through stable oxime bond conjugation. FIGS. 4a and 4b illustrate the strategy to rewire cell surfaces for the goal of cell adhesion to self-assembled monolayers (SAMs) of alkanethiolates on gold substrates. Employing microfluidic oxidation[48] and lithography,[49] aldehyde and oxyamine SAMs, respectively, were patterned at a ratio of 10%. The remaining 90% of the surface was backfilled with tetra(ethylene glycol) alkanethiol, which is known to pacify biomaterials against nonspecific protein adsorption and cell adhesion.[50] Meanwhile, fbs were cultured separately with keto- (5) and oxyamine-LUVs (6, 3 mM, 4 h), resulting in membrane fusion and subsequent display of ketones (9) and oxyamines (10) from cell surfaces. The resulting ketone- and oxyamine-presenting fbs were then seeded (~$10^2$ cells/mL, 2 h) to the patterned oxyamine and aldehyde substrates, respectively, and allowed to react and form stable oxime linkages in the patterned regions. The cells were cultured for 4 d on these substrates, growing and proliferating in the patterned regions. The results of patterned keto-fbs on oxyamine SAMs are shown in FIG. 4c; patterned oxy-fbs on aldehyde SAMs are displayed in FIGS. 4d and 4e. Furthermore, unmodified cells did not attach to the surface. Thus, this strategy allows for a bottom-up, bio-orthogonal synthetic approach to rewire how cells adhere to materials and does not require metabolic or genetic cell manipulations.

Flow cytometry. Flow cytometry was performed to further verify the ability of tailoring small molecules to cell surfaces through covalent oxime bond formation. This method also enables the quantification of ketone and oxyamine molecules that are present at the cell surface after liposome delivery and subsequent membrane fusion. Liposomes that incorporated varying oxyamine concentrations of (i.e., 0, 1, 5, and 10 mol %) were generated (6, 3 mM) cultured with separate fb populations for 4 h, resulting in membrane fusion and oxyamine display (10, FIG. 5a). A ketone-modified fluorescein dye (7, 0.15 mM, 2 h) was then conjugated to the cell surfaces in each population, producing green fluorescently labeled fbs. The FACS analyses results are demonstrated in FIG. 5b. Twenty thousand cells were counted for all samples. As shown, the fluorescence intensity increases with increasing number of oxyamine molecules present for fluorescein conjugation. Additionally, the control cell population that was fused with unmodified liposomes and reacted with ketone-fluorescein (7) demonstrated the lowest intensity. Furthermore, a bead with known FITC molecule density was calibrated and used as a standard comparison to quantify the number of oxyamine molecules present at the cell surface after fusion.[51] FIG. 5c displays the correlation between oxyamine mol % and oxyamine molecules per cell counted by FACS analyses. The calculated molecules per cell for the control fbs and oxyamine-presenting fbs that were fused with 1%, 5%, and 10% oxyamine were approximately 128, 1300, 9800, and 17400, respectively. A linear trend was observed; as the molecule concentration increased, the fluorescence intensity and number of molecules at the cell surface increased. Thus, the density of molecules that decorate cell surfaces can be controlled and quantified using this liposome fusion-based methodology for cell-surface engineering.

Figure 6:
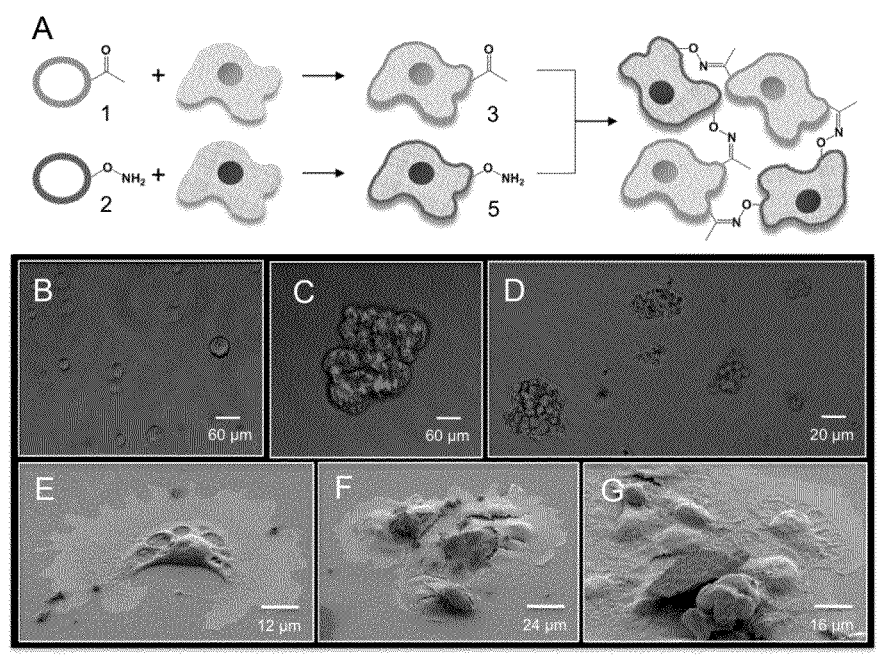
FIG. 6 shows fluorescent, phase contrast, and scanning electron micrographs (SEM) describing 3D spheroid formation via liposome fusion and chemoselective cell-surface tailoring. Two fb populations were cultured separately with ketone- (1) or oxyamine- (2) containing liposomes, resulting in membrane fusion and subsequent tethering of ketones and oxyamines from the cell surface. The oxyamine-tethered rat2 fibroblasts (12) contained a fluorescent m-cherry nuclear label. The ketone-presenting Swiss albino 3T3 fibroblasts (9) were not fluorescently labeled. (A) Two fibroblast populations were cultured separately with ketone- (1) or oxyamine- (2) containing liposomes. Due to the presence of a positively charged liposome, fusion occurred producing ketone- (9) and oxyamine- (12) tethered cells. Upon mixing these cell populations, clustering and tissue-like formation, based on chemoselective oxime conjugation, occurred. (B) Control experiments (overlay image) demonstrate no spheroid formation for cells that did not contain either ketone or oxyamine groups. (C and D) However, when two cell populations displaying ketone (9) and oxyamine (12) recognition groups are mixed, interconnected spheroid assemblies form (overlay images). (E-G) Representative SEM images of (E) control cells and (E and F) spheroid assemblies, as described above, are displayed. For all spheroid assemblies depicted, cell populations were mixed and cultured together for 3 h before imaging at ~$10^4$ cells/mL.

3D spheroid assembly. The ability to generate multicellular connected tissues of multiple cell types in vitro is useful for studying the complex interplay of cells in a range of organs in vivo and for developing strategies for synthetic tissue transplantation. With varying successes, a number of current strategies to generate 3D cell connections rely on forcing mixed cell populations into complex microfabricated wells or vessels. Therefore, in the present liposome fusion technology, an oxime-based strategy was used to generate 3D spheroid assemblies of interconnected cells using two different cell-type populations (FIG. 6). The oxyamine-presenting rat2 fbs (10) contained a nuclear m-cherry fluorescent label so that the cell clustering to non-fluorescent ketone-tethered cells (9) could be easily observed. During a 3-hour period of mixed-culturing (~$10^4$ cells/mL) in solution, cells formed spheroid structures due to the presence of complementary recognition groups (FIGS. 6C and 6D). Furthermore, when oxyamine-presenting fbs (10) were cultured with control fbs (cells not functionalized with ketone groups), spheroid assembly did not occur (FIG. 6B). Studies were also performed to test whether spheroid size and cell composition could be controlled. Ketone-presenting hMSCs (11) were co-cultured with oxyamine-functionalized fbs (10) for 1, 2, 3, and 5 h. After 1 h, clusters comprised only with a few cells were observed. As the co-culturing duration was increased, larger spheroid structures were observed. Notably, control experiments were performed simultaneously to ensure that spheroid generation was being directed through chemoselective oxime conjugation. Tissue structure formation did not occur without the proper complementary pair displayed from cell surfaces, regardless of the mixing duration (1-5 h). Thus, size and composition of 3D cell assemblies in solution could be controlled, showing great promise for applications in stem cell transplantation and regenerative medicine.

Spheroid formation was also characterized by scanning electron microscopy (SEM) (FIG. 6E-G). Cells functionalized with oxyamine (10) and ketone (9) groups were able to generate clusters when mixed in solution, as displayed in FIGS. 6F and 6G. However, spheroid assemblies were not observed when ketone-presenting fbs were reacted with non-functionalized cells; fbs spread out on the surface, migrated, but remained alone (FIG. 6E). Notably, cells were able to form stable, interconnected 3D structures in solution simply upon mixing two tailored cell populations. Currently, methods to generate these structures require the support of a 3D hydrogel matrix and/or assisted assembly through an external stimulus.[5,7-9,13]

Figure 7:
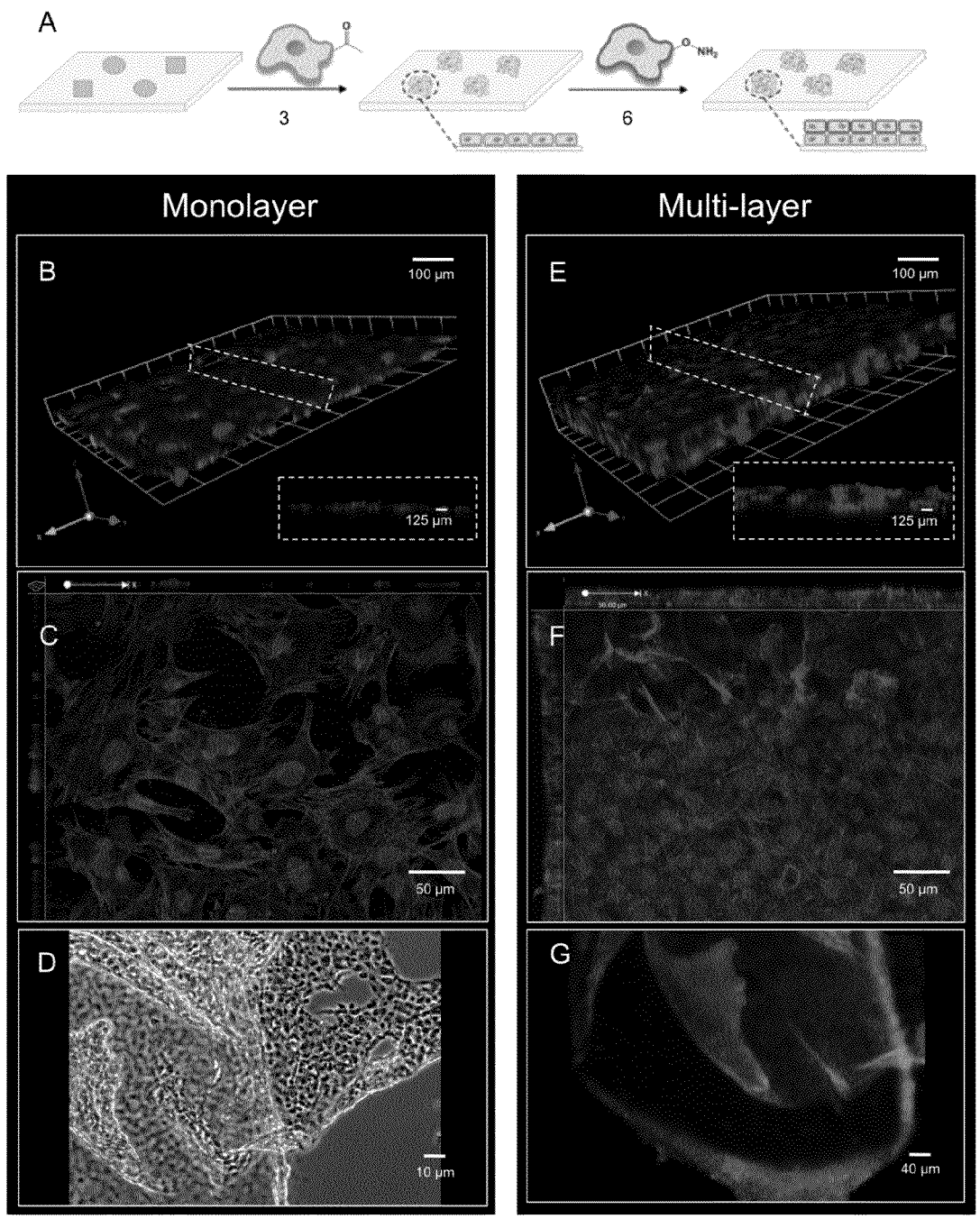
FIG. 7 shows a general schematic and images of oxime-mediated, 3D tissue-like structure formation with controlled interconnectivity. (A) Ketone- (1) and oxyamine- (2) containing liposomes were added to two separate fb populations, resulting in membrane fusion and subsequent presentation of the ketone (9) and oxyamine (12) groups from cell surfaces. By culturing these cells on substrates, alternating cell population seeding layer-by-layer gave rise to multi-layered, tissue-like cell sheets through stable oxime chemistry. (B) A 3D reconstruction and (C) confocal micrograph showing only a monolayer of cells after oxyamine-presenting cells (12) were cultured with adhered non-functionalized cells. (E) A 3D reconstruction and (F) confocal micrograph of multiple cell layers after oxyamine-presenting cells (12) were added to substrates presenting ketone-containing cells (9). (D and G) Intact, 3D multi-layered cell sheets can be removed from the surface by gentle agitation as displayed by brightfield and fluorescent images. The insets in B and E show a z-plane cross-section that indicates the thickness of the cell layers. Cells were stained with DAPI (nucleus) and phalloidin (actin).
Figure 8:
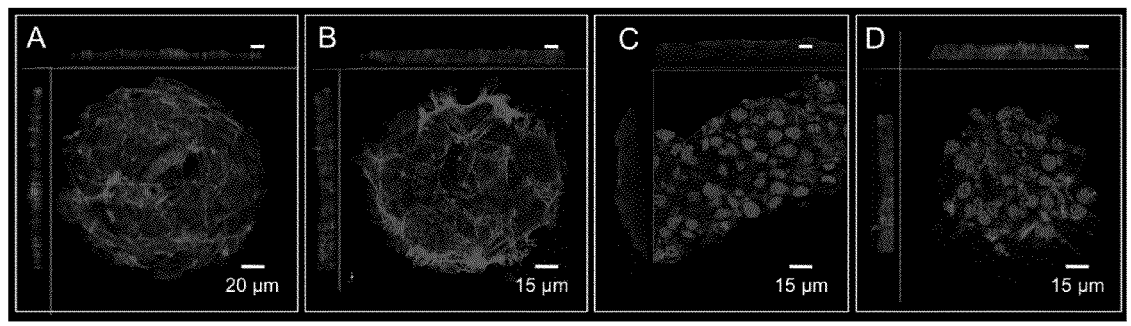
FIG. 8 shows confocal images representing 2D monolayer and 3D multi-layered tissue-like structures of fbs with spatial control. (A) A circular, 2D monolayer of fbs (control) results after ketone-functionalized fbs (9) and fbs (not functionalized with oxyamines) were patterned on a circular, microcontact printed region, presenting fibronectin, and allowed to grow for 5 days. (B-D) Fbs, functionalized with ketone groups (9) were seeded onto microcontact printed regions containing fibronectin and allowed to grow for 2 days. Fbs, functionalized with oxyamine groups (12) were then seeded and allowed to grow for 2-3 more days. Confocal images demonstrating 3D tissue formation in (B) circle, (C) bar, and (D) square geometries are depicted. The corresponding z-plane cross-sections that indicate the thickness of the cell layers are shown as an inset; scale bars represent 30 µm. Cells were stained with DAPI (nucleus) and phalloidin (actin).

3D multi-layered tissues. In addition to forming small, 3D cell clusters or spheroid structures in solution, this strategy may be employed to direct larger, dense 3D tissue-like networks on a surface with geometric control. Full substrates were used (FIG. 7), as well as surfaces that were patterned with cell adhesive and non-adhesive regions to generate multi-layered sheets and patterned tissue structures (FIG. 8), respectively.[52] Ketone- (1) and oxyamine-(2) tailored liposomes were cultured with separate fb populations, resulting in membrane fusion and subsequent presentation of chemoselective sites for oxime conjugation from the surface (9 and 10, respectively) (FIG. 7A). Culturing these groups on a solid support (~$10^5$ cells/mL) and in a layer-by-layer deposition manner gave rise to multi-layered, tissue-like cell sheets, which were characterized by confocal microscopy, as shown in FIGS. 7E and 7F. Fbs naturally only form a single monolayer once they become contact-inhibited. However, fb-fb clustering has been successfully induced though oxime-mediated, cell-surface engineering based on liposome fusion.

To ensure that oxime chemistry was aiding in the formation of 3D tissue-like structures, several control experiments were performed. Cells that did not present ketone or oxyamine functionality were seeded onto separate surfaces. A second cell population presenting oxyamine (6) or ketone (3) groups from the cell surface was added, resulting in the formation of only a 2D monolayer of cells (FIGS. 4B and 4C). Similarly, two different cell populations that were tethered with oxyamine (10) groups were mixed together, and only a 2D monolayer was generated after 4 d of culture. The same results were observed after culturing two different ketone-functionalized cell populations (9) for 4 d. These results further support the hypothesis that multi-layered cell interconnectivity is driven by complementary, oxime chemistry. This strategy was also extended toward the generation of 3D multi-layered co-cultures with hMSCs and fbs. Ketone-functionalized hMSCs (11) were first cultured on a substrate (~$10^5$ cells/mL), and stem cells were allowed to spread out and grow for 2 d. Oxyamine-presenting fbs (12) were then added (~$10^5$ cells/mL) and co-cultured for an additional 2 d. 3D Multi-layered cell sheets (4 layers) were formed. The proper controls were conducted; without the oxime pair, only a 2D monolayer of stem cells and fbs was formed.

3D tissue release and cell viability. During multi-layer culture, it was possible to control the release of the tissues from the surface with gentle agitation (FIGS. 7D and 7G). The ability to release tissue after surface-supported growth in vitro shows great potential for applications in tissue engineering and cellular transplantation. Cell viability was also tested for 3D spheroid and multi-layered structures of fbs and hMSC/fb co-cultures using the trypan blue assay.[53] After spheroid (1, 2, 3, and 5 hours of mixing in solution) and multi-layer (3, 5, and 7 days on a surface) formation, cells were incubated with trypan blue (0.4%, 2 min). Viability was 100% for all cells in the spheroid assemblies (1-5 hours) and multi-layer structure at day 3. After 5 and 7 days of multi-layer generation, cells showed an approximate viability of 91% and 84%, respectively. The blue intensity (fluorescence false colored for enhanced visualization) was compared to a control cell population by linescan analysis. The control cells were cultured for 7 days to generate 3D multi-layers and were then fixed. Trypan blue was allowed to react for 2 min, followed by imaging and quantification. Overall, the viability of cells in conducting membrane fusion to generate 3D tissue-like structures in solution and on a solid support is high. Therefore, this method may be very useful for applications in tissue engineering and stem cell transplantation.

3D tissue patches with geometrical control. Spatial control was demonstrated by generating a number of 3D multi-cellular micropatterns. Microcontact printing[52] was used to produce a variety of patterns and geometries on a gold substrate. Employing SAM and microfabrication technologies, hexadecanethiol (1 mM in EtOH) was printed on a gold surface. The surface was then backfilled with $EG_4$ (1 mM in EtOH, 16 h) to render the remaining regions inert to nonspecific protein absorption. Fibronectin, a cell-adhesive protein, was then added (10 mg/mL in CBS, 2 h), adhering only to the hydrophobic, patterned areas. As shown by the confocal image in FIG. 8A, only a 2D, circular cell pattern arises after ketone-presenting fbs (9) were cultured with fbs, not functionalized with oxyamine molecules. However, when liposome fusion occurs to display complementary ketone and oxyamine groups from cell surfaces (9 and 10, respectively), multi-layered 3D cell patterns were formed (FIG. 8B-D). Circular, bar, and square circular tissue-like structures are depicted in FIG. 8B-D. The ability to generate 3D tissues with controlled geometry would find great use in tissue transplantation, in which specifically tailored patches are required.

Figure 9:
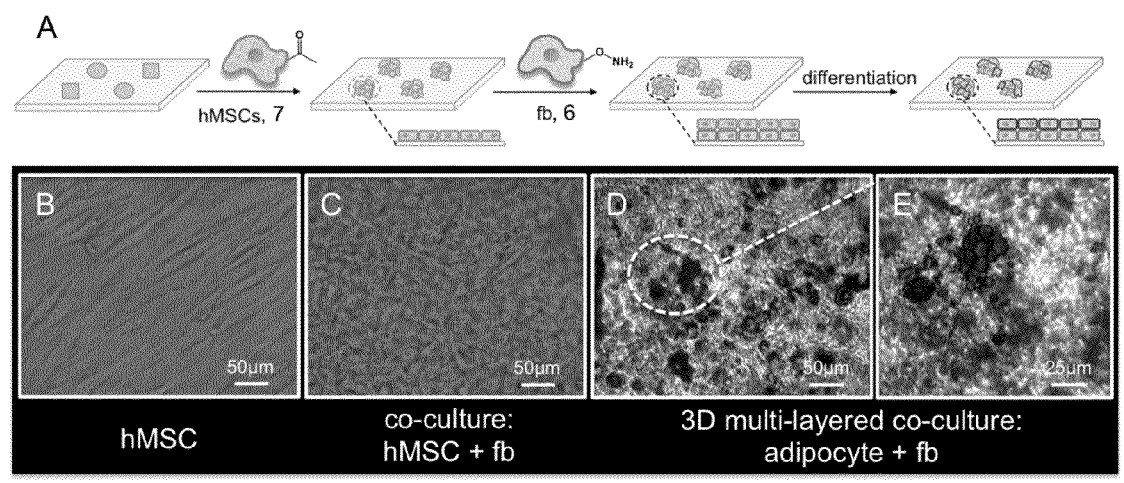
FIG. 9 shows general schematic and brightfield images representing oxime-mediated, 3D tissue-like structure formation with hMSC/fb co-cultures and subsequent induced adipocyte differentiation to generate 3D adipocyte/fb co-culture structures. (A) Ketone-tethered human mesenchymal stem cells (hMSCs) (11) were seeded onto a surface, followed by the addition of oxyamine-functionalized fbs (12). The co-culture was allowed to grow and divide for 3 d at which point adipogenic differentiation was induced with the addition of the appropriate media. This resulted in a 3D multi-layer of adipocytes and fbs. (B) A confluent 2D monolayer of ketone-presenting hMSCs is represented. (C) A brightfield image displaying a 3D multi-layer co-culture of hMSCs (11) and oxyamine-functionalized fbs (12) is shown. (D) Adipogenic differentiation was induced with media resulting in 3D multi-layered adipocyte and fb co-culture structures, represented by low and (E) high-resolution brightfield images (after 10 days in culture). Adipocytes were stained with Oil Red 0 (lipid vacuoles) and Harris Hemotoxylin (nucleus).

3D stem cell co-cultures with induced adipocyte differentiation. The general use of the present liposome fusion method was explored to delivered ketone and oxyamine groups to different cell lines, and it was demonstrated that 3D spheroid and multi-layer can be generated using co-cultures of hMSCs and fbs. The methodology was next extended toward stem cell differentiation to determine whether 3D multi-layered co-cultures could be induced to generate tissues of differentiated hMSCs and fbs. As shown in FIG. 9A, ketone-functionalized hMSCs (11) were first cultured on a substrate for 3 d, producing a 2D monolayer of cells (FIG. 9B). Oxyamine-tethered fbs (12) were then co-cultured with the hMSCs, and the cells were allowed to grow and proliferate for 2 d (FIG. 9C). Adipogenic induction media was then added, the 3D multi-layered co-culture was stained for nuclei and lipid vacuoles, which are characteristic of adipocytes (fat cells). The phase contrast images in FIGS. 9D and 9E demonstrate the successful generation of tissue-like structures, comprising induced adipocytes and fbs. The ability to co-culture stem cells with many other cell types and induce differentiation shows great promise in the field of regenerative medicine and stem cell transplantation.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Full Citations for Documents Referred to in the Specification
1. Nelson, C. M.; Bissel, M. *J. Annu. Rev. Cell Dev. Biol.* 2006, 22, 287-309.
2. Meshel, A. S.; Wei, Q.; Adelstein, R. S.; Sheetz, M. P. *Nat. Cell Biol.* 2005, 7, 157-164.
3. Isenberg, B. C.; Williams, C.; Tranquillo, R. T. *Annu. Biomed. Eng.*, 2006, 34, 971-985.

4. Hollister, S. J. (2005). *Nature Mater.* 4:518-524.
5. Gillette, B. M.; Jensen, J. A.; Tang, B.; Yang, G. J.; Bazargan-Lari, A.; Zhong, M.; Sia, S. K. *Nat. Mater.* 2008, 7, 636-640.
6. Tanaka, H.; Murphy, C. L.; Murphy, C.; Kimura, M.; Kawai, S.; Polak, J. M. *J. Cell Biochem.* 2004, 93, 454-462.
7. Gartner, Z. J.; Bertozzi, C. R. *Proc. Natl. Acad. Sci. U.S.A.* 2009, 106, 4606-4610.
8. Albrecht, D. R.; Underhill, G. H.; Wassermann, T. B.; Sah, R. L.; Bhatia, S. N. *Nat. Methods* 2006, 3, 369-375.
9. Gray, D. S.; Tan, J. L.; Voldman, J.; Chen, C. S. *Biosens. Bioelectron.* 2004, 19, 1765-1774.
10. Odde, D. J, Renn, M. J. *Biotechnol. Bioeng.* 2000, 67, 312-318.
11. Nahmias, Y.; Odde, D. J. *Nat. Protocol* 2006, 1, 2288-229626.
12. Barron, J. A.; Krizman, D. B.; Ringeisen, B. R. *Annu. Biomed. Eng.* 2005, 33, 121-130.
13. Inaba, R.; Khademhosseini, A.; Suzuki, H.; Fukuda, J. *Biomaterials* 2009, 30, 3573-3577.
14. Ringeisen, B. R.; Othon, C. M.; Barron, J. A.; Young, D.; Spargo, B. *J. Biotechnol.* 2006, 1, 930-948.
15. Chiou, P. Y.; Ohta, A. T.; Wu, M. C. *Nature* 2005, 436, 370-372.
16. Falconnet, D.; Csucs, G.; Grandin, H. M.; Textor, M. *Biomaterials* 2006, 27, 3044-3063.
17. Khademhosseini, A.; Langer, R.; Borenstein, J.; Vacanti, J. P. *Proc. Natl. Acad. Sci. U.S.A.* 2006, 103, 2480-2487.
18. Luo, W.; Chan, E. W. L.; Yousaf, M. N. *J. Am. Chem. Soc.* 2010, 132, 2614-2621.
19. Mahal, L. K.; Yarema, K. J.; Bertozi, C. R. *Science* 1997, 276, 1125-1128.
20. Prescher, J. A.; Bertozzi, C. R. *Nat. Chem. Biol.* 2005, 1, 13-21.
21. Chen, I.; Howarth, M.; Lin, W.; Ting, A. Y. *Nat. Methods* 2005, 2, 99-104.
22. Keppler, A.; Pick, H.; Arrivoli, C.; Vogel, H.; Jonhsson, K. *Proc. Natl. Acad. Sci. U.S.A.* 2004, 101, 9955-9959.
23. Miller, L. W.; Sable, J.; Goelet, P.; Sheetz, M. P.; Cornish, V. W. *Angew. Chemie. Int. Ed.* 2004, 43, 1672-1675.
24. Kellam, B.; De Bank, P. A.; Shakesheff, K. M. *Chem. Soc. Rev.* 2003, 32, 327-337.
25. Rabuka, D.; Forstner, M. B.; Grovers, J. T.; Bertozzi, C. R. *J. Am. Chem. Soc.* 2008, 130, 5947-5953.
26 Mayer, A. (2002) Membrane fusion in eukaryotic cells. *Annu. Rev. Cell. Develop. Biol.* 18, 289.
27. Rowan, A. (2006) Clamping down on exocytosis. *Nat. Rev. Mol. Cell. Biol.* 7, 555-561.
28. Ellens, H., Bentz, J., and Szoka, F. C. (1985) Proton- and calcium-induced fusion and destabilization of liposomes. *Biochemistry,* 24, 3099-3106.
29. Dennison, S. M., Greenfield, N., Lenard, J., and Lentz, B. R. (2002) VSV Transmembrane domain (TMD) peptide promotes PEG-mediated fusion of liposomes in a conformationally sensitive fashion. *Biochemistry,* 41, 14925-14934.
30. Evans, K. 0., and Lentz, B. R. (2002) Kinetics of lipid rearrangements during poly(ethylene glycol)-mediated fusion of highly curved unilamellar vesicles. *Biochemistry,* 41, 1241-1249.
31. Jahn, R., Lang, T., and Sudhof, T. C. (2003) Membrane fusion. *Cell,* 112, 519-533.
32. McNew, J. A., Weber, T., Parlati, F., Johnston, R. J., Melia, T. J., Sollner, T. H., and Rothman, J. E. (2000) Close is not enough: Snare-dependent membrane fusion requires an active mechanism that transduces force to membrane anchors. *J. Cell Biol.* 150, 105-117.
33. Soolner, T. H. (2004) Intracellular and viral membrane fusion: An uniting mechanism. *Curr. Opin. Biol.* 16, 429-435.
34. Parlati, F., Weber, T., McNew, J. A., Westermann, B., Sollner, T. H., and Rothman, J. E. (1999) Rapid and efficient fusion of phospholipid vesicles by the α-helical core of a SNARE complex in the absence of an N-terminal regulatory domain. *Proc. Natl. Acad. Sci. U.S.A.* 96, 12565-12570.
35. Paumet, F., Rahimian, V., and Rothman, J. E. (2004) The specificity of SNARE-dependent fusion is encoded in the SNARE motif. *Proc. Natl. Acad. Sci. U.S.A.* 101, 3376-3380.
36. Richard, A., Marchi-Artzner, V., Lalloz, M-N., Brienne, M-J., Artzner, F., Gulik-Krzywicki, T., Guedeau-Boudeville, M-A., and Lehn, J.-M. (2004) Fusogenic supramolecular vesicle systems induced by metal ion binding to amphiphilic ligands. *Proc. Natl. Acad. Sci. U.S.A.* 101, 15279-15284.
37. Marchi-Artzner, V., Gulik-Krzywicki, T., Guedeau-Boudeville, M-A., Gosse, C., Sanderson, J. M., Dedieu, J.-C., and Lehn, J-M. (2001) Selective adhesion, lipid exchange and membrane-fusion processes between vesicles of different sizes bearing complementary molecular recognition groups. *ChemPhysChem* 2, 367-376.
38. Marchi-Artzner, V., Jullien, L., Gulik-Krzywicki, T., and Lehn, J.-M. (1997) Molecular recognition induced aggregation and fusion between vesicles containing lipids bearing complementary hydrogen bonding head groups. *Chem. Commun.* 1, 117-118.
39. Paleos, C. M., and Tsiourvas, D. (2006) Interaction between complementary liposomes: A process leading to multicompartment systems formation. *J. Mol. Recognition,* 19, 60-67.
40. Chan, Y.-H. M., Lengerich, B., and Boxer, S. G. (2009) Effects of linker sequences on vesicle fusion mediated by lipid-anchored DNA oligonucleotides. *Proc. Nat. Acad. Sci. U.S.A.* 106, 979-984.
41 Gong, Y., Luo, Y., and Bong, D. (2006) Membrane activation: Selective vesicle fusion via small molecule recognition. *J. Am. Chem. Soc.* 128, 14430-14431.
42. Wilson, J. T.; Krishnamurthy, V. R.; Cui, W.; Qu, Z.; Chaikof, E. L. *J. Am. Chem. Soc.* 2009, 131, 18228-18229.
43. Csiszar, A.; Hersch, N.; Dieluweit, S.; Biehl, R.; Merkel, R.; Hoffmann, B. *Bioconjugate Chem.* 2010, 21, 537-543.
44. Pale-Grosdemange, C., Simons, E. E., Prime, K. L., and Whitesides, G. M. (1991) Formation of self-assembled monolayers by chemisorption of derivatives of oligo(ethylene glycol) of structure $HS(CH_2)_{11}(OCH_2CH_2)_mOH$ on gold *J. Am. Chem. Soc.* 113, 12-20.
45. Park, S., and Yousaf, M. N. (2008) *Langmuir,* 24, 6201-6207.
46. Csiszar, A., Hersch, N., Dieluweit, S., Biehl, R., Merkel, R., and Hoffmann, B. (2010) Novel fusogenic liposomes for fluorescent cell labeling and membrane modification. *Bioconjugate Chem.* 21, 537-543.
47. Beigel, M., Keren-Zur, M., Laster, Y., and Loyter, A. (1988) Poly(aspartic acid)-dependent fusion of liposomes bearing the quaternary ammonium detergent [[[(1,1,3,3-tetramethylbutyl)cresoxy]ethoxy]ethyl]dimethylbenzyl ammonium hydroxide. *Biochemistry* 1988, 27, 660-666.
48. Westcott, N. P., Pulsipher, A., Lamb, B. M., and Yousaf, M. N. (2008) Expedient generation of patterned surface aldehydes by microfluidic oxidation for chemoselective immobilization of ligands and cells. *Langmuir,* 24, 9237-9240.

49. Lamb, B. M., Barrett, D. G., Westcott, N. P., and Yousaf, M. N. (2008) Microfluidic lithography of SAMs on gold to create dynamic surfaces for directed cell migration and contiguous cell cocultures. *Langmuir*, 24, 8885-8889.
50. Harder, P., Grunze, M., Dahint, R., Whitesides, G. M., and Laibinis, P. E. (1998) Molecular conformation in Oligo (ethylene glycol)-terminated self-assembled monolayers on gold and silver surfaces determines their ability to resist protein adsorption. *J. Phys. Chem. B*, 102, 426-436.
51. Hsiao, S.C., Shum, B. J., Onoe, H., Douglas, E. S., Gartner, Z., Mathies, R. A., Bertozzi, C. R., and Francis, M. B. (2009) Direct cell surface modification with DNA for the capture of primary cells and the investigation of myotube formation on defined patterns. *Langmuir*, 25, 6985-6991.
52. Love, J. C.; Estroff, L. A.; Kriebel, J. K.; Nuzzo, R. G.; Whitesides, G. M. *Chem. Rev.* 2000, 105, 1103-1170.
53. Hsiao, S.C.; Shum, B. J.; Onoe, H.; Douglas, E. S.; Gartner, Z.; Mathies, R. A.; Bertozzi C. R.; Francis, M. B. *Langmuir* 2009, 25, 6985-6991.

I claim:

1. A mixture comprising a plurality of liposomes of type A and a plurality of liposomes of type B, wherein the liposomes of type A comprise a reactive functional group that reacts with a reactive functional group comprised in the liposomes of type B to form a covalent chemical interaction that results in the adhesion of the liposomes of type A and the liposomes of type B.

2. The mixture of claim 1, wherein the reactive functional group in the liposomes of type A and the reactive functional group in the liposomes of type B are complementary, bio-orthogonal pairs of reactive functional groups.

3. The mixture of claim 2, wherein the complementary, bio-orthogonal pairs of reactive functional groups are selected from:
   (1) ketones and oxyamines which react to form an oxime;
   (2) ketones and hydrazines which react to form a hydrazone;
   (3) dienes and dienophiles which react to form a six membered ring (Diels Alder reaction); and
   (4) azides and alkynes which react to form a triazole (Huisgen reaction).

4. The mixture of claim 3, wherein the complementary, bio-orthogonal pair of reactive functional groups are ketones and oxyamines which react to form an oxime.

5. The mixture of claim 1, wherein the reactive functional group is comprised in an amphiphatic molecule wherein the reactive functional group is located in the hydrophilic portion of the molecule.

6. The mixture of claim 5, wherein the reactive functional group forms the hydrophilic portion of the amphiphatic molecule and the lipophilic portion of the amphiphatic molecule is a long hydrocarbon chain, optionally comprising one or more double bonds.

7. The mixture of claim 6, wherein the amount of the amphiphatic molecule comprising a reactive functional group in the liposomes of type A and B is about 1 mol % to about 10 mol.

8. The mixture of claim 1, wherein the liposomes of type A and B, independently comprise about 1 mol % to about 10 mol % of an amphiphatic molecule comprising a reactive functional group, about 90 mol % to about 99 mol % of a neutral lipid and, optionally, about 1mol % to about 5 mol % of a charged lipid.

9. The mixture of claim 1, wherein the liposomes of type A and type B independently further comprise functional molecules so that when the liposomes of type A and type B are fused, a physical change occurs.

10. The mixture of claim 9, wherein the functional molecules are fluorescent indicator molecules.

11. The mixture of claim 9, wherein the functional molecules are dyes and the physical change is a change in color.

12. A method for promoting adhesion of liposomes comprising contacting a plurality of liposomes of type A with a plurality of liposomes of type B, wherein the liposomes of type A comprise a reactive functional group that reacts with a reactive functional group comprised in the liposomes of type B to form a covalent chemical interaction that results in the adhesion of the liposomes of type A and the liposomes of type B.

* * * * *